(12) United States Patent
Paldus et al.

(10) Patent No.: US 11,859,161 B2
(45) Date of Patent: Jan. 2, 2024

(54) METHOD OF CARRYING OUT A BIOREACTION WITH MULTIPLE COUPLED VESSELS

(71) Applicant: Finesse Solutions, Inc., Santa Clara, CA (US)

(72) Inventors: Barbara Paldus, Woodside, CA (US); Mark Selker, Los Altos Hills, CA (US)

(73) Assignee: Finesse Solutions, Inc., Santa Clara, CA (US)

( * ) Notice: Subject to any disclaimer, the term of this patent is extended or adjusted under 35 U.S.C. 154(b) by 0 days.

(21) Appl. No.: 17/677,517

(22) Filed: Feb. 22, 2022

(65) Prior Publication Data
US 2022/0169964 A1 Jun. 2, 2022

Related U.S. Application Data

(62) Division of application No. 15/427,613, filed on Feb. 8, 2017, now Pat. No. 11,292,999.
(Continued)

(51) Int. Cl.
*C12M 1/00* (2006.01)
*C12M 3/00* (2006.01)
(Continued)

(52) U.S. Cl.
CPC ............ *C12M 23/02* (2013.01); *C12M 23/40* (2013.01); *C12M 23/44* (2013.01); *C12M 23/58* (2013.01);
(Continued)

(58) Field of Classification Search
CPC ...... C12M 23/02; C12M 23/40; C12M 23/44; C12M 23/58; C12M 25/06; C12M 27/00;
(Continued)

(56) References Cited

U.S. PATENT DOCUMENTS 6,121,042 A   9/2000   Peterson
6,642,019 B1  11/2003  Anderson
(Continued)

FOREIGN PATENT DOCUMENTS

CN       1557947 A    12/2004
CN     102296029 A    12/2011
(Continued)

OTHER PUBLICATIONS

Database WPI, 0, Derwent World Patents Index, vol. 2013, No. 64, Database accession No. 2013-P38640, XP002777210 & CN202881248U.
(Continued)

*Primary Examiner* — Lydia Edwards
(74) *Attorney, Agent, or Firm* — MINTZ LEVIN COHN FERRIS GLOVSKY AND POPEO, P.C.

(57) ABSTRACT

A method of carrying out a bioreaction in a multivessel bioreactor system may include flowing a culture medium at an initial flow rate through one or more fluidic paths between a master vessel and one or more slave vessels, detecting a first culture medium parameter value in the master vessel or the slave vessels, transmitting the first culture medium parameter value to a control system, determining an adjusted flow rate of the culture medium at the control system based on the first culture medium parameter value, and controlling a bidirectional fluid transfer device with the control system to adjust the flow rate of the culture medium through the one or more fluidic paths. The control system may adjust the flow rate of the culture medium to maintain a substantially uniform value of the first culture medium parameter value in the master vessel or the one or more slave vessels.

13 Claims, 9 Drawing Sheets

Related U.S. Application Data

(60) Provisional application No. 62/381,283, filed on Aug. 30, 2016.

(51) Int. Cl.

| | |
|---|---|
| *B01L 3/00* | (2006.01) |
| *C12M 1/02* | (2006.01) |
| *C12M 1/34* | (2006.01) |
| *C12M 1/06* | (2006.01) |
| *C12M 3/06* | (2006.01) |
| *C12M 1/12* | (2006.01) |
| *C12M 1/26* | (2006.01) |

(52) U.S. Cl.
CPC ............ *C12M 25/06* (2013.01); *C12M 27/00* (2013.01); *C12M 27/02* (2013.01); *C12M 27/16* (2013.01); *C12M 29/10* (2013.01); *C12M 29/16* (2013.01); *C12M 29/18* (2013.01); *C12M 33/14* (2013.01); *C12M 41/12* (2013.01); *C12M 41/26* (2013.01); *C12M 41/44* (2013.01)

(58) Field of Classification Search
CPC ...... C12M 27/02; C12M 27/16; C12M 29/10; C12M 29/16; C12M 29/18; C12M 33/14; C12M 41/12; C12M 41/26; C12M 41/44
See application file for complete search history.

(56) References Cited

U.S. PATENT DOCUMENTS

| | | |
|---|---|---|
| 2008/0068920 A1 | 3/2008 | Galliher |
| 2010/0261226 A1 | 10/2010 | Niazi |
| 2011/0136225 A1 | 6/2011 | Vuniak-Novakovic et al. |
| 2012/0231528 A1 | 9/2012 | Muller-Feuga et al. |
| 2016/0017280 A1 | 1/2016 | Villiger-Oberbek et al. |
| 2016/0145563 A1 | 5/2016 | Berteau et al. |
| 2016/0177252 A1 | 6/2016 | Peters |

FOREIGN PATENT DOCUMENTS

| | | |
|---|---|---|
| CN | 202881248 U | 4/2013 |
| CN | 104130929 A | 11/2014 |
| CN | 105713224 A | 6/2016 |
| WO | 2015/003012 | 1/2015 |
| WO | 2015/068450 | 5/2015 |

OTHER PUBLICATIONS

Carneau, et al., "Evaluation of a Single-Use Bioreactor for the Fed-Batch Production of a Monoclonal Antibody," BioPharminternational.com, Nov. 2, 2010, 4 pp. [www.biopharminternational.com/evaluation-single-use-bioreactor-fed-batch-production-monoclonal-antibody] retrieved Jan. 31, 2018.
Cascaval, D., et al., "Modeling of mixing times for stirred bioreactors. 3. Mixing time for aerated broths," Chem. Ind., vol. 56, No. 12, 2002, DD. 506-513.
Chisti, Y., "Animal cell culture in stirred bioreactors: observations on scale-up," Bioprocess Engineering, Oct. 1993, vol. 9, No. 5, pp. 191-196.
De Wilde, D., et al., "Superior scalability of single-use bioreactors," Sep. 23, 2014, BioProcess International, 6 pp.
GE Healthcare Life Sciences Data file 29/0929-25 AA "Xcellerex™ XDR cell culture bioreactor systems," Feb. 2014.
Humphrey, A., "Shake flask, to fermentor: what have we learned?" Biotechnology Progress, vol. 14, 1998, DD. 3-7.
Jones, N., "Single-Use Processing for Microbial Felmentations," Apr. 14, 2015, BioProcess International, 8 pp. [www.bioprocessintl.com/upstream-processing/fermentation/single-use-processinq-for-microbial-fermentations/1 retrieved Jan. 31, 2018.
Ju L.-K., et al., Improved scale-up strategies of bioreactors, Bioprocess Engineering vol. 8, 1992, DD. 49-53.
Lara, A., et al., Living with heterogeneities in bioreactors, Lara et al., Molecular Biotechnology, vol. 34, 2006, pp. 355-381.
Li, J., et al. "Challenges of scale down model for disposable bioreactors: case studies on growth & product quality impacts", in Single-Use Technologies: Bridging Polymer Science to Biotechnology Applications, ECI Symposium Series, Leesburg, VA, Oct. 18-21, 2015. [http://dc.engconfintl.org/biopoly/38].
Oosterhuis, N. M. G., "Scale-up of bioreactors," PhD Thesis, Delft University of Technology, Delft, 1984.
Slavik, A., "Mixing problems with many tanks," The Mathematical Association of America, Nov. 2013, pp. 806-821. <http://dx.doi.org/10.4169/amer.math.monthly.120.09.806>.
Smith, C., "Scaling Up Your Cell cultures to Bioreactors," Jul. 14, 2014, 5 pp. [www.biocompare.com/Editorial-Articles/165203-Scaling-Up-Your-Cell-cultures-to-Bioreactors/: retrieved Jan. 31, 2018.
Stoker, E., "Comparative studies on scale-up methods of single-use bioreactors," Utah State University, Masters Thesis, 2011. [https://dig italcommons. usu .ed u/etd/889].
Votruba, J., et al., "Physiological similarity and bioreactor scale-up," Folia Microbiology, vol. 37, No. 5, 1992, pp. 331-345.
Whitford, W., et al., "Considerations in scale-up of viral vaccine production," Sep. 1, 2011, BioProcess International, 12 pp. [www.bioprocessintl.com/manufacturing/antibody-non-antibody/considerations-in-scale-up-of-viral-vaccine- production-320990/] retrieved Jan. 31, 2018.
Xing, Z., et al., "Scale-up analysis for a CHO cell culture process in large-scale bioreactors," Biotechnology and Bioengineering, vol. 103, No. 4, Jul. 1, 2009, p. 733-746.
BioSep Acoustic Perfusion System product information, by Applikon Biotechnology, product known as of Aug. 30, 2016. [www.applikon-bio.com/en/news2/itemlist/category/52-biosep] retrieved Jan. 31, 2018.
Kleenpak™ Sterile Connectors product information, by Pall Corporation, product known as of Aug. 30, 2016. [www.pall.com/main/biopharmaceuticals/product.page?id=34125] retrieved Jan. 31, 2018.
KR2i TFF System® product information, by Spectrum Labs, product known as of Aug. 30, 2016. [www.spectrumlabs.com/filtration/KR2System. html] retrieved Jan. 31, 2018.
Kuhner shaker SB200-X (OrbShake) product information, by Kuhner Technology, product known as of Aug. 30, 2016. [www.kuhner.com/en/product/shakers/single-use/sb200-x.html] screenshots retrieved Jan. 31, 2018.
Mobius® Bioreactors product information, by Millipore Sigma (Merck), product known as of Aug. 30, 2016. [www.emdmillipore.com/US/en/mobius-single-use-manufacturing/mobius-single-use-bioreactors/mobius-bioreactors/fCyb.qB.1 TkAAAFEF9sMfopc,nav] retrieved Jan. 31, 2018.
ReadyMate Single-Use Connectors product information, GE Healthcare Life Sciences, product known as of Aug. 30, 2016. [https://www.gelifesciences.com/shop/liquid-preparation- and-management/single-use-connectors/readymate-single-use-connectors-p-00257?current=28936612] retrieved Jan. 31, 2018.
Scale Up-New Definitions & Challenges, by Infors HT, product known as of Aug. 30, 2016. [http://www.infors-ht.com/index.php/en/applications/scale-up] retrieved Jan. 31, 2018.
Database WPI Week 201364, Thomson Scientific, London GB, AN 2013-P38640, XP-002777210 & CN 202 881 248 U Apr. 17, 2013, 1 p.
EP17188616.1, Extended European Search Report dated Jan. 22, 2018, 10 pp.
Singapore Office Action dated Apr. 21, 2020, issued in SG Application No. 10201706817V.

From ATCC Animal Cell Culture Guide
www.atcc.org

METHOD OF CARRYING OUT A BIOREACTION WITH MULTIPLE COUPLED VESSELS

CROSS-REFERENCE TO RELATED APPLICATION

This application is a divisional of U.S. application Ser. No. 15/427,613, filed Feb. 8, 2017, now U.S. Pat. No. 11,292,999, which claims benefit under 35 U.S.C. 119(e) to U.S. Provisional Patent Application No. 62/381,283, filed Aug. 30, 2016, and titled "BIOREACTOR WITH MULTIPLE COUPLED VESSELS", which are incorporated herein by specific reference in their entirety and for all purposes.

BACKGROUND

Scale-up of bioreactors or the systematic attempt to increase the size (volume) of the bioreactor while maintaining titer (end product yield), has been a subject of study almost as long as the modern bioreactor has been in use. Typical bioprocess development follows a standard path of laboratory scale where basic screening and base level (e.g., media) optimization are carried out, pilot plant scale-up where generally larger bioreactors are used and further optimization is carried out, and finally plant or production scale where larger volumes are utilized to make the end product economically. The process of scale-up is often necessary in production as the cells are expanded (their number increased), and they are moved to successively larger and larger bioreactors. A modern (2014) single-use "seed train" or process train in bioprocess manufacturing is shown in FIG. 1 (Superior Scalability of Single-Use Bioreactors, Davy De Wilde, Thomas Dreher, Christian Zahnow, Ute Husemann, Gerhard Greller, Thorsten Adams and Christel Fenge, Sep. 23, 2014 BioProcess International Magazine). The range from a 1 mL vial to a 1000 L stirred tank bioreactor (STR) is a $10^6$ increase in volume and far beyond the linear or constant range for the physical parameters in a single vessel.

In single-use bioreactors, which are by their very nature smaller in volume than their stainless steel counterparts (<2000 L vs. <50,000 L+), the desire for a clear and consistent scale-up path still exists as evidenced by the continuing numbers of papers published (e.g., *Scale-up Analysis for a CHO Cell Culture Process in Large-Scale Bioreactors*, Xing et al., Biotechnology and Bioengineering, vol. 103, (4), p. 722, Jul. 4, 2009) and student theses (*Comparative Studies on Scale-Up Methods of Single-Use Bioreactors*, Emily Stoker, Utah State University, Ph.D. Thesis 2011) dedicated to this subject; both references incorporated herein by reference in their entireties. This literature highlights the fact that fundamental physical laws do not allow the scaling of bio-processes parameters to be simple or direct. Thus, researchers have been motivated to apply great scrutiny and attention to how to effectively scale-up a bioprocess. In fact, these issues have even motivated researchers and workers in the field to look at scale-up by scale-down (Oosterhuis, N. M. G., "Scale-up of Bioreactors," PhD Thesis, Delft University of Technology, Delft (1984), incorporated herein by reference in its entirety).

SUMMARY

An aspect of the disclosure pertains to a bioreactor system that may be characterized by the following features: (a) two or more fluidically coupled vessels configured to collectively carry out a bioreaction; (b) one or more fluidic paths coupling the two or more vessels to one another, where the fluidic paths are configured to provide flow of culture medium between the two or more vessels during the bioreaction; (c) one or more fluid transfer devices along at least some of the one or more fluidic paths; and (d) a control system. In various embodiments, the control system is configured to (i) read or receive values of one or more parameters characterizing the culture medium in one or more of the vessels during the bioreaction, (ii) use the values to determine an adjusted flow rate in at least one of the fluidic paths to maintain substantially uniform values of the one or more parameters in the culture medium from vessel-to-vessel among the two or more vessels, and (iii) control at least one of the fluid transfer devices to adjust the flow rate determined in (ii). In certain embodiments, each of the fluidic paths is configured to permit bidirectional flow of the culture medium between two of the vessels. In certain embodiments, the two or more vessels are arranged in closed loop. In certain embodiments, the two or more vessels and the one or more fluidic paths provide the bioreactor system in a star configuration.

A related aspect of the disclosure pertains to a bioreactor system that may be characterized by the following features: (a) two or more fluidically coupled vessels configured to collectively carry out a bioreaction; (b) one or more fluidic paths coupling the two or more vessels to one another, where fluidic paths are configured to provide flow of culture medium between the two or more vessels during the bioreaction; (c) one or more fluid transfer devices along at least some of the one or more fluidic paths; and (d) a control system. In many implementations, the control system is configured to (i) read or receive values of one or more parameters characterizing the culture medium in one or more of the vessels during the bioreaction, and (ii) control the one or more fluid transfer devices to transfer the culture medium between the two or more vessels, via the one or more fluidic paths, such that the time required to exchange the culture medium in the two or more vessels is at most about one-tenth the time required for cells in the vessels to double under conditions in the two or more vessels. In certain embodiments, each of the fluidic paths is configured to permit bidirectional flow of culture medium between two of the vessels. In certain embodiments, the two or more vessels are arranged in closed loop. In some implementations of the above aspects, the one or more parameters include a parameter selected from the group consisting of pH, temperature, a cell metabolite concentration, and dissolved oxygen concentration of the culture medium.

The bioreactor system of the above aspects may include at least one more fluidically coupled vessel for a total of three or more fluidically coupled vessels configured to collectively carry out the bioreaction. In some implementations, the bioreactor system includes five or more fluidically coupled vessels, including the two or more vessels.

In any of the disclosed embodiments, each vessel may have a working volume of not greater than about 500 liters, or not greater than about 100 liters, or not greater than about 50 liters. In any of the disclosed embodiments, the ratio of total working volume of the two or more vessels to the working volume of largest of the two or more vessels is at least about 3. In some implementations, the two or more vessels include polymeric vessel walls.

In some implementations, one of the two or more vessels is a master vessel and the others are satellite vessels. In such implementations, the master vessel may include a mixing system configured to agitate the culture medium. The mixing system may include a device such as an impeller, an orbital shaker, a wave rocker, and a plunger. In some designs, one or more of the satellite vessels does not include a mixing system. In some embodiments, the master vessel includes one or more sensors for the pH, temperature, a cell metabolite concentration, and dissolved oxygen in the culture medium. In some embodiments, the master vessel has a larger working volume than any of the satellite vessels.

In some designs of the bioreactor system, the two or more vessels are provided on one or more scales and/or load cells to monitor their masses during the bioreaction. In such designs, the control system may be further configured to: read or receive at least one output of the one or more scales and/or load cells, as at least one of the values of one or more parameters; and based on the outputs of the scales and/or load cells, control the one or more of fluid transfer devices to transfer the culture medium between the two or more vessels such that a volume of the culture medium in the two more vessels is controlled.

In certain embodiments, the fluidic paths include tubing and aseptic connectors attached to the two or more vessels. In some cases, the fluidic paths attach proximate to bottoms of the two or more vessels. In some cases, at least one of the fluid transfer devices includes a pump.

The control system may be configured to maintain particular parameter values within certain bounds. It may also be configured to maintain the parameter values at a consistent level from vessel-to-vessel. In some implementations, the control system is configured to adjust conditions in the two or more vessels to ensure that the mean pH of the culture medium in the two or more vessels does not vary from one vessel to another by more than about 0.1. In some implementations, the control system is configured to adjust conditions in the two or more vessels to ensure that shear forces experienced by cells in the two or more vessels are substantially equal from one vessel to another during the bioreaction. In certain embodiments, the control system is configured to adjust conditions in the two or more vessels to ensure that culture medium gas transfer rates in the two or more vessels are substantially equal from one vessel to another during the bioreaction.

The bioreactor system may also be designed such that the variance (or standard deviation) in a parameter value is minimized or at least kept within a defined bound in any of the vessels. For example, the two or more vessels and the control system may be configured such that the pH of the culture medium within any of the vessels has variance of at most about 0.1 pH units. In certain embodiments, the control system is a proportional-integral-derivative controller.

In certain bioreactor systems of this disclosure, the control system includes a single control loop that is configured to control a master vessel. In such cases, one of the two or more vessels is the master vessel and the others are satellite vessels. The master vessel may have a mixing system configured to agitate the culture medium.

In various embodiments, bioreactor system and/or one or more of its vessels is configured to operate in a perfusion mode. In accordance with such embodiments, at least one of the two or more fluidically coupled vessels includes a fluidic inlet and a fluidic outlet, and the bioreactor system is configured to introduce the culture medium to the at least one vessel through the fluidic inlet, exchange the culture medium in the vessel while retaining the biological cells in that vessel, and flow the culture medium out the fluidic outlet. In some such perfusion embodiments, the fluidic outlet includes a filter configured to prevent the biological cells in the at least one vessel from leaving the at least one vessel and the fluidic outlet. In some embodiments, one of the two or more vessels is a master vessel configured to provide culture media to the at least one vessel through the fluidic inlet to provide perfusion. In some perfusion embodiments, the control system and master vessel are together configured to substantially maintain defined values of dissolved oxygen concentration, temperature, and pH in the culture medium in the master vessel and in the at least one vessel. As with some other embodiments providing master and satellite vessels, the master vessel may include a mixing system, while the at least one vessel does not include a mixing system. In some embodiments, a vessel configured to operate in perfusion mode includes one or more microcarriers, hollow fibers, and/or adhesion plates. In some embodiments, two or more vessels are configured to operate in perfusion mode. For example, at least two of the two or more fluidically coupled vessels each include a fluidic inlet and a fluidic outlet and the bioreactor system is configured to introduce the culture medium to the at least two vessels through the fluidic inlet, exchange the culture medium in the vessel while retaining the biological cells in that vessel, and flow the culture medium out the fluidic outlet.

Another aspect of the disclosure provides methods of carrying out a bioreaction in a bioreactor system that may be characterized by the following operations: (i) two or more fluidically coupled vessels configured to collectively carry out a bioreaction; (ii) one or more fluidic paths coupling the two or more vessels to one another, where the one or more fluidic paths are configured to provide flow of culture medium between the two or more vessels during the bioreaction; and (iii) one or more fluid transfer devices along at least some of the one or more fluidic paths, where each of the fluidic paths is configured to permit bidirectional flow of the culture medium between two of the vessels, and/or the two or more vessels are arranged in closed loop. The methods may be characterized by the following operations: (a) reading or receiving values of one or more parameters characterizing the culture medium in one or more of the vessels during the bioreaction; (b) using the values to determine an adjusted flow rate in at least one of the fluidic paths to maintain substantially uniform values of the one or more parameters in the culture medium from vessel-to-vessel among the two or more vessels, and (c) controlling at least one of the fluid transfer devices to adjust the flow rate determined in (b).

In another aspect, the disclosure provides methods of carrying out a bioreaction in a bioreactor system including: (i) two or more fluidically coupled vessels configured to collectively carry out the bioreaction; (ii) one or more fluidic paths coupling the two or more vessels to one another, where the one or more fluidic paths are configured to provide flow of culture medium between the two or more vessels during the bioreaction; and (iii) one or more fluid transfer devices along at least some of the one or more fluidic paths, where each of the fluidic paths is configured to permit bidirectional flow of the culture medium between two of the vessels, and/or the two or more vessels are arranged in closed loop. The methods may be characterized by the following operations: (a) reading or receiving values of one or more parameters characterizing the culture medium in one or more of the vessels during the bioreaction, and (b) controlling the one or more fluid transfer devices to transfer the culture medium between the two or more vessels, via the one or more fluidic paths, such that the time required to exchange the culture medium in the two or more vessels is at most about one-tenth the time required for cells in the vessels to double under conditions in the two or more vessels.

In the above method aspects, the bioreactor system may include at least one more fluidically coupled vessel for a total of three or more fluidically coupled vessels configured to collectively carry out the bioreaction. In some of the method implementations, the bioreactor system includes four or more fluidically coupled vessels, including the two or more vessels. In the above method aspects, the one or more parameters include pH, temperature, a cell metabolite concentration, and/or dissolved oxygen concentration of the culture medium.

In certain embodiments, the methods further include adjusting conditions in the two or more vessels to ensure that the mean pH of the culture medium in the two or more vessels does not vary from one vessel to another by more than about 0.1. In certain embodiments, the methods further include adjusting conditions in the two or more vessels to ensure that shear forces experienced by cells in the two or more vessels are substantially equal from one vessel to another during the bioreaction. In certain embodiments, the methods further include adjusting conditions in the two or more vessels to ensure that culture medium gas transfer rates in the two or more vessels are substantially equal from one vessel to another during the bioreaction.

In certain method embodiments, each vessel of the bioreactor system has a working volume of not greater than about 500 liters or not greater than about 50 liters. In certain embodiments, the ratio of total working volume of the two or more vessels to the working volume of largest of the two or more vessels is at least about 3.

In certain method embodiments, one of the two or more vessels is a master vessel and the others are satellite vessels, where the master vessel includes a mixing system configured to agitate the culture medium. In some implementations, one or more of the satellite vessels does not include a mixing system. In some implementations, the master vessel has a larger working volume than any of the satellite vessels.

In some of the method aspects of this disclosure, the method additionally includes: reading or receiving at least one output of one or more scales and/or load cells, on which the two or more vessels are provided; and based on the outputs of the scales and/or load cells, controlling the one or more of fluid transfer devices to transfer the culture medium between the two or more vessels such that a volume of the culture medium in the two more vessels is controlled. In certain embodiments, the fluidic paths include tubing and aseptic connectors attached to the two or more vessels. In some cases, the at least one of the fluid transfer devices includes a pump.

In some of the disclosed methods, at least one of the one of the two or more fluidically coupled vessels includes a fluidic inlet and a fluidic outlet. In such cases, the method additionally includes introducing the culture media to the at least one vessel through the fluidic inlet, flowing the culture media over biological cells while they are retained in the at least one vessel, and flowing the culture media out the fluidic outlet, to thereby operate the at least one vessel in a perfusion mode. When operating in perfusion mode, a vessel may make use of a filter configured to prevent the biological cells in the at least one vessel from leaving the at least one vessel and the fluidic outlet. Alternatively or in addition, a vessel may additionally include micro-carriers, hollow fibers, and/or adhesion plates for retaining cells. In certain embodiments, one of the two or more vessels is a master vessel configured to provide culture media to the at least one vessel through the fluidic inlet to provide perfusion. In such cases, a method may substantially maintain defined values of dissolved oxygen concentration, temperature, and pH in the culture medium in the master vessel and in the at least one vessel.

Another aspect of this disclosure pertains to methods of scaling a bioprocess working volume from that of a small-scale bioreactor to that of a large-scale bioreactor. In certain embodiments, such methods are characterized by the following operations: (a) determining process conditions for performing the bioprocess in a test vessel having a relatively small working volume (e.g., no greater than about 700 liters), where the process conditions include test values of one or more parameters characterizing culture medium in the vessel during the bioprocess; (b) designing a bioreactor system including a control system and two or more fluidically connected production vessels, each having a working volume of not greater than about 1.5 times the working volume of the test vessel, and the sum of the working volumes of the two or more production vessels being at least about 2 times larger than the working volume of the test vessel; and (c) constructing and/or arranging the two or more production vessels and the control system as specified in (b) to produce the large-scale bioreactor. Thereafter, the bioprocess may be performed in the large-scale bioreactor. Designing the bioreactor system may include designing the control system to (i) read or receive production values of the one or more parameters characterizing the culture medium in one or more of the two or more vessels during the bioprocess, (ii) use the read or received production values to determine an adjusted flow rate of the culture medium between the two or more production vessels to maintain substantially uniform production values of the one or more parameters in the culture medium from vessel-to-vessel among the two or more production vessels during the bioprocess, and (iii) control one of the fluid transfer devices disposed between the two or more production vessels to adjust the flow rate as determined in (ii). In certain embodiments, the bioreactor system is configured to permit bidirectional flow of the culture medium between two of the production vessels, and/or the two or more production vessels are arranged in closed loop.

In certain embodiments, the bioreactor system includes three or more production vessels configured to collectively carry out the bioprocess. In certain embodiments, the bioreactor system includes four or more production vessels configured to collectively carry out the bioprocess. In certain embodiments, the bioreactor system includes five or more production vessels configured to collectively carry out the bioprocess. In certain embodiments, the bioreactor system includes six or more production vessels configured to collectively carry out the bioprocess. In certain embodiments, each production vessel has a working volume of not greater than about 500 liters. In certain embodiments, the ratio of total working volume of the two or more production vessels to the working volume of largest of the two or more production vessels is at least about 3.

Designing the bioreactor system may involve designing the control system to maintain, during the bioprocess, the production values of the one or more parameters to be substantially equal to the test values of the one or more parameters. In some implementations, the one or more parameters include pH, temperature, a cell metabolite concentration, or dissolved oxygen concentration of the culture medium. In some implementations, the method involves designing the control system to adjust conditions in the two or more production vessels to ensure that the mean pH of the culture medium in the two or more production vessels does not vary from one vessel to another by more than about 0.1 pH units.

Recognizing that one or more of the individual vessels may have a turn down ratio, the performing the bioprocess may unfold as follows: (d) conducting the bioprocess at a first total working volume of culture medium in the large-scale bioreactor constructed in (c); and (e) after (d), conducting the bioprocess at a second total working volume of culture medium that is greater than the first total working volume but still uses only the two or more production vessels of the large-scale bioreactor. In a variation, performing the bioprocess may unfold as follows: (d) conducting at least a portion of the bioprocess in the large-scale bioreactor constructed in (c); and (e) after (d), adding or activating one more additional production vessels to the large-scale bioreactor and at least partially filling the one or more additional production vessels with culture medium from one or more other production vessels of the large-scale bioreactor. In another variation, performing the bioprocess may unfold as follows: (d) conducting the bioprocess in the large-scale bioreactor constructed in (c); and (e) after (d), removing one or more of the two or more production vessels containing culture medium and cells grown in the culture medium. In some implementations, the cells were cultivated during the bioprocess are grown for treating a patient.

In some implementations, one of the production vessels is a master vessel and the others are satellite vessels, and the master vessel includes a mixing system configured to agitate the culture medium. The satellite vessels need not include a mixing system. The master vessel may include one or more sensors for the pH, temperature, a cell metabolite concentration, and dissolved oxygen in the culture medium. Typically, though not necessarily, the master vessel has a larger working volume than any of the satellite vessels.

Another aspect of this disclosure pertains to bioreactor systems designed or configured to operate in a perfusion mode. Some such systems may be characterized by the following features: (a) two or more fluidically coupled vessels configured to collectively carry out a bioreaction, where at least one of the vessels is a perfusion vessel having a fluidic inlet, a fluidic outlet, and a filter or other cell retaining structure configured to prevent biological cells from leaving the perfusion vessel during the bioreaction; (b) one or more fluidic paths coupling the two or more vessels to one another, where the one or more fluidic paths are configured to provide flow of culture medium between the two or more vessels during the bioreaction; (c) one or more fluid transfer devices (e.g., pumps) along at least some of the one or more fluidic paths; and (d) a control system configured to introduce the culture media to the perfusion vessel through the fluidic inlet, exchange the culture medium in the vessel while retaining the biological cells in that vessel, and flow the culture media out the fluidic outlet, to thereby operate in a perfusion mode. Examples of cell retaining structures include, in addition to filters, micro-carriers, hollow fibers, and adhesion plates. Any of these may be disposed within a perfusion vessel.

The control system may additionally be configured to (i) read or receive values of one or more parameters characterizing the culture medium in one or more of the vessels during the bioreaction, (ii) use the values to determine an adjusted flow rate in at least one of the fluidic paths to maintain substantially uniform values of the one or more parameters in the culture medium from vessel-to-vessel among the two or more vessels, and (iii) control at least one of the fluid transfer devices to adjust the flow rate determined in (ii).

In some perfusion embodiments, one of the two or more vessels is a master vessel configured to provide culture media to the perfusion vessel through the fluidic inlet to provide perfusion. In some cases, the control system and master vessel are together configured to maintain values of dissolved oxygen concentration, temperature, and pH in the culture medium in the master vessel and in the perfusion vessel. The master vessel may include a mixing system, while, in some cases, the perfusion vessel does not include any mixing system.

The bioreactor system is not limited to embodiments having only a single perfusion vessel. For example, the system may include a second fluidically coupled vessels perfusion vessel including its own fluidic inlet, fluidic outlet, and cell retention structure configured to prevent biological cells from leaving during the bioreaction. In some cases, the system employs a second perfusion vessel that is initially fluidically unconnected to the two or more fluidically connected vessels. However, the second perfusion vessel includes a supplemental fluidic connection for connecting to the bioreactor system after the bioreactor system has been operating in perfusion mode.

In some implementations, the bioreactor system is configured to at least partially fill the perfusion vessel with culture medium from one or more other vessels during the bioreaction. In some implementations, the perfusion vessel is configured to be removed from the bioreactor system, along with the perfusion vessel's culture medium and cells grown in the culture medium, before the bioreaction completes.

These and other features of the disclosure will be described in more detail below with reference to the associated drawings.

DESCRIPTION

Figure 1:
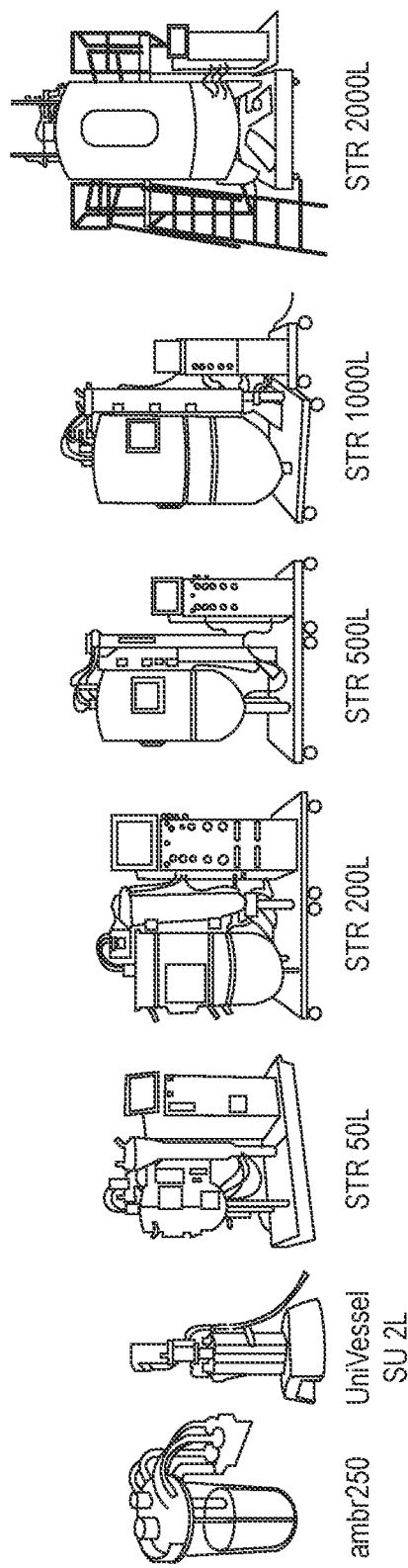
FIG. 1. Prior art scale-up train of single-use bioreactors from a 2014 publication.

Certain details of scale-up processes and the complications experienced by workers in this field are described in, for example, *Physiological Similarity and Bioreactor Scale-up*, Votruba et al., Folia Microbiology, vol 37 (5), p. 331, 1992, *Shake Flask, to Fermentor: What Have We Learned*, Humphrey, Biotechnology Progress, vol. 14, p. 3, 1998, and Living With Heterogeneities in Bioreactors, Lara et al., Molecular Biotechnology, vol. 24, p. 355, 2006, each incorporated herein by reference in its entirety. It has been suggested by many authors and summarized by Ju (*Improved scale-up strategies of bioreactors*, Bioprocess Engineering vol. 8, p. 49, 1992 all information incorporated herein) that in order to effectively scale-up a bioprocess the following process characteristics would be maintained as constant:

1. Reactor geometry;
2. The volumetric oxygen transfer coefficient $k_L a$ (m/s m$^2$/m$^3$);
3. Maximum shear experienced by cells (kg/m$^2$ s);
4. Power input per unit volume of liquid P(kW)/V (m$^3$);
5. Volumetric gas flow rate per unit volume of liquid Q (m$^3$/s)/V(m$^3$)
6. Superficial gas velocity v (m/s)
7. Mixing time (s)
8. Impeller Reynolds Number $R_{ei}$=fluid density×impeller speed×(density Impeller tip speed)$^2$/kinematic viscosity (dimensionless quantity)
9. Momentum factor (cm$^3$/s)

Item 1 refers to the actual shape and aspect ratio (height vs. width) of the bioreactor. This has a large effect on how the bioreactor functions and the extent to which it can be only partially filled (e.g.: the bioreactor's operational range in fill volume or turn-down ratio). Additional parameters related to the bioreactor shape and size are the impeller designs and ratio of their diameters to the diameter of the bioreactor. Item 2 refers to the rate at which oxygen can be transferred to the media—typically from sparged oxygen or air. In general, there is a tradeoff between making the bubbles smaller (increased surface area to volume ratio with decreased size due to their spherical shape) and foaming that occurs from the surface tension of the high number density of breaking bubbles. Item 3 and Item 4 are related to the shear force that will actually damage a cell. Mammalian cells are far more susceptible to this type of damage than bacterial cells. Shear forces are induced by many things including the surface tension of a bubble bursting or from a vortex formed at the tip of the impeller (*Animal Cell Culture in Stirred Bioreactors: Observations on Scale-up*, Y. Christi, Process Biochemistry, vol. 28, 0. 511, 1992). Items 5 and 6, like item 2 are related to the ability to transfer gas into or out of the media. Item 7, mixing time, refers to the time it takes a bioreactor to reach a set degree of uniformity in concentration of one or more monitored analytes or cell density. The set degree can differ in the literature, but a typical definition is that the concentration differs by less than 10% at any point in the bioreactor. The mixing time can also be defined as the time it takes for a parameter (or tracer) to be homogeneously distributed within the bioreactor to the level required for a successful process. (*Modeling of mixing times for stirred bioreactors*. 3. *Mixing time for aerated broths*, D. Cascaval et al, Chem. Ind. Vol. 56 (12), p 506, 2002) incorporated herein by reference in its entirety. Unless otherwise stated herein, this last definition will be used herein. Item 8, the impeller Reynolds number is inversely related to the mixing time of the bioreactor. Generally speaking, the higher Reynolds number, the higher the turbulence but the shorter the mixing time. The cost for shorter mixing times is higher shear; this is another tradeoff that must be balanced for the exact system under study. Item 9, apparently less frequently used in the literature, is the momentum factor and is related to both shear and mass transfer in the bioreactor.

The number of process parameters and combination of process parameters from the above list that are desired to be held constant during scaling changes based on a large number of considerations. These considerations include but are likely not limited to: the cell line chosen, the type or product being produced, the yield required from the product, the type of bioreactor used, the details of the process implemented, and the degree of scale-up desired. It can be gleaned from the brief review of the aforementioned literature that scale-up is not generally a simple process and has occupied the time and efforts of many skilled workers in the field of bioproces sing for many years.

For the process to maintain a consistent yield and be clinically and economically viable, the cells/process must minimize, or at worst maintain, bioreactor heterogeneity of the above parameters (and sometimes related parameters) during the scale-up process. As mentioned above, this is to date a significant challenge even for those skilled in this art. This often results in lower titer or cell density for the end of a seed train than for the small scale bioreactors in the laboratory. Ideally then, a system by which the volume can be scaled up without changing the bioreactor scale would yield optimal results and allow straightforward changes from R&D through production. This is in contrast with scale-up and scale-down today where most of the optimization work is performed to match the titer and productivity of small glass vessels (<15 L) at the production volumes envisaged (biocompare.com/Editorial-Articles/165203-Scaling-Up-Your-Cell-cultures-to-Bioreactors/), and where scalability inconsistencies are still being observed in both titer and product quality as a result of the different bioreactor volumes [J. Li, G. Zhang, et al. "Challenges of scale down model for disposable bioreactors: case studies on growth & product quality impacts", Single-Use Technologies, Leesburg, VA, Oct. 18-21, 2015 (incorporated herein by reference in its entirety) or infors-ht.com/index.php/en/applications/scale-up]. Similarly, the performance of new large-scale bioreactors is always compared to running the same process in a glass vessel (Pall Application Note: USD2926, "Cultivation of CHO Cells in Allegro™ STR 200 Single-Use Stirred Tank Bioreactor System," incorporated herein by reference in its entirety or biopharminternational.com/evaluation-single-use-bioreactor-fed-batch-production-monoclonal-antibody).

The embodiments described here address many of these challenges. Current conventional (e.g., stirred tank) bioreactor design at this time can practically speaking allow scalability/turn-down ratio of up to a factor of 5 [GE Healthcare Life Sciences Data file 29-0929-25 AA "Xcellerex™ XDR cell culture bioreactor systems" (incorporated herein by reference in its entirety) or emdmillipore.com/US/en/mobius-single-use-manufacturing/mobius-single-use-bioreactors/mobius-bioreactors/fCyb.qB.1TkAAAFEF9sMfopc,nav or bioprocessintl.com/upstream-processing/fermentation/single-use-processing-for-microbial-fermentations/1. As mentioned above, the terminology often used in the bioprocessing industry is "turn-down ratio" or the ratio from the maximum working volume to the minimum working volume. For example, then, a single-use bioreactor properly designed could scale from 130 L to 650 L with a 5:1 turndown ratio. The goal for design of the turn-down ratio is that within this scaling, many of the 9 criteria mentioned above can be considered "conserved" or similar enough that the cell densities, cell viabilities, and titers are will be the same; specifically, for a bioreactor with a 5:1 turn-down ratio at any volume from 20% to 100% of the working volume (maximum usable volume) one can consider the properties of the bioreactor very similar. However, if it is desired to scale-up past the maximum volume, to date, a new larger bioreactor would be required to increase the total number of cells or the titer. As discussed earlier, a larger bioreactor cannot generally be treated as having the same 9 aforementioned quantities, thus creating the problem discussed above. For example, mixing time is not preserved in a 2000 L bioreactor between full volume and half-volume operation (Thermo Fischer 2000 L SUB Scale-up Summary or Sub Validation guide page 41/42, incorporated herein by reference). Note that when micro-carriers or other suspension mechanisms are introduced into a bioreactor, the scale-up problem is significantly more difficult (bioprocessintl.com/manufacturing/antibody-non-antibody/considerations-in-scale-up-of-viral-vaccine-production-320990/). Furthermore, with certain types of shear-sensitive cells such as stem cells, scale-up is paramount to producing the cellular product.

One method to circumvent this issue is to simultaneously run multiple, or N, bioreactors of the same size to scale-up the volume. This is, however, often considered an unsatisfying or even unacceptable way to do scale-up as each bioreactor is independent and can have slightly different conditions and must be set up independently. This means that each bioreactor is controlled separately (e.g., each has its own set of PID loop controllers), and therefore the batches from each bioreactor are considered to be independent, namely, different from a yield, traceability, quality, and general behavior perspective. Furthermore, in order to eventually utilize the N bioreactors' products as one batch, the contents must be combined or "pooled" before being processed in the downstream (e.g.: filtration, chromatography, virus inactivation). Quality groups and/or regulatory bodies often object to pooling as this creates a lack of traceability to the source of any issues (e.g.: contamination, lower yield or efficacy etc.). Given these facts, the concept of running N independent (smaller) bioreactor vessels is often eschewed for scale-up in favor of one much larger bioreactor.

Certain embodiments of this disclosure provide a way to circumvent, or at least significantly mitigate the aforementioned problems of scale-up by introducing coupling between the N bioreactors; here coupling means the physical transfer of the contents (cells and supernatant) between the bioreactors. This can be viewed as an extension to a very well-known set of problems in mathematics called "mixing problems". If one couples a set of N bioreactors together by exchanging fluid contents between them such as to allow the contents of all of the N bioreactors to be considered homogenous (and therefore identical), we have for all intents and purposes, one batch. This allows multiple bioreactors to be utilized to create one batch without pooling while bypassing the scale-up issues and without the need for scrutiny from a quality or regulatory group Going back to the issue of coupling the bioreactors, we will review the mathematical machinery of mixing between tanks. As an introduction to the concept of mixing in tanks we will start with a simple and common problem—single analyte (e.g., brine or salt) mixing. The most basic problem usually has one tank partially filled with an analyte (e.g., salt) dissolved in water. Typical problems require one to work out the solution to an ordinary differential equation (ODE) and calculate how long will it take for the system to reach equilibrium. The typical problem also requires one to calculate the eventual equilibrium concentration of the analyte for a given influx at a stated rate and concentration of analyte in water with given initial concentrations and volume.

Figure 2:
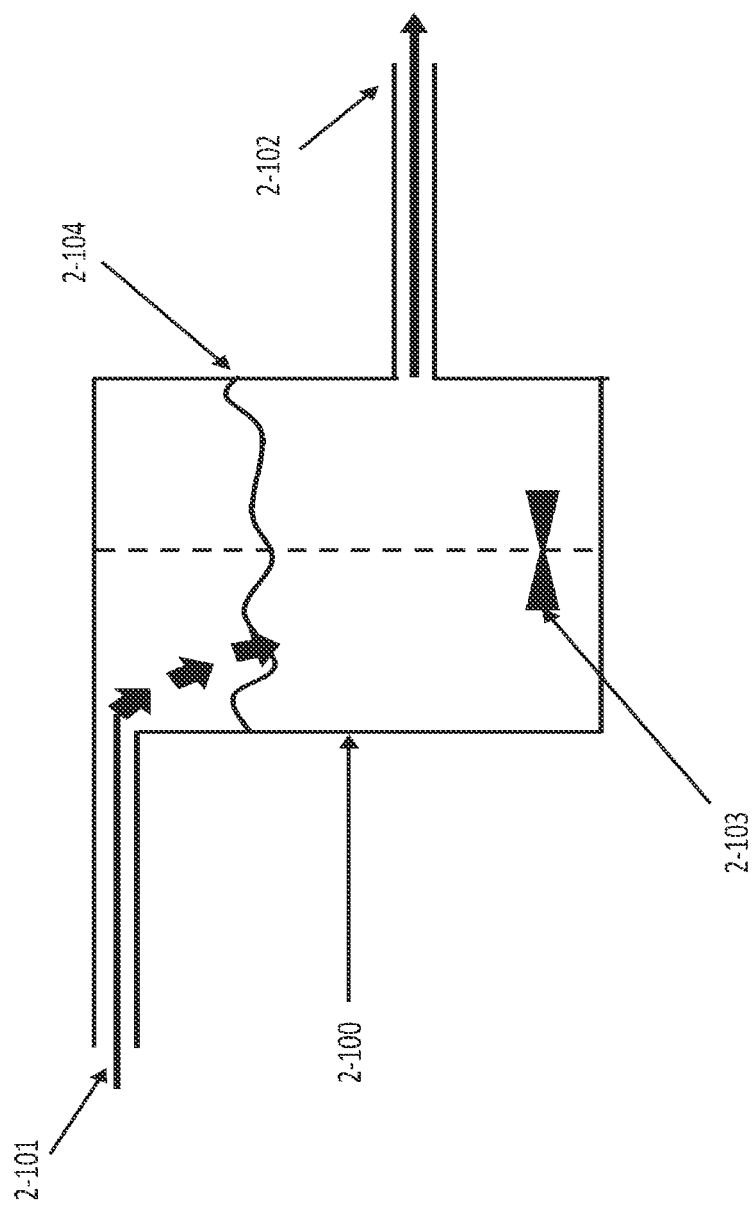
FIG. 2. A simple tank introducing the differential equations that describe mixing.

FIG. 2 shows a mixing tank with a situation similar to that described above. Assume:
  $S(t)$ is the amount of salt at time t;
  $V(t)$ is the solution volume in the tank at time t;
  $F_{In}$ is the flow rate at which the solution flows into the tank;
  $F_{Out}$ is the flow rate at which the mixture flows out of the tank;
  $C_{in}$ is the concentration of salt in the solution flowing into the tank;
  $C_{out}$ is the concentration of salt in the solution flowing out of the tank;
  $R_{in}$ is the rate at which salt is poured into the tank $$R_{in} = F_{In} R_{In} \times C_{in} \qquad \text{Equation 1}$$

$R_{out}$ is the rate at which the salt is poured out of the tank $$R_{out} = F_{out} R_{out} \times C_{out} \qquad \text{Equation 2}$$

Given these assumptions, we can define:

$$C_{out}(t) = S(t)/V(t) \qquad \text{Equation 3}$$

$$dS(t)/dt = \text{the rate of change of salt in the tank as } R_{in} - R_{out} \qquad \text{Equation 4}$$

This can be re-stated as:

$$dS(t)/dt = F_{In} \times C_{in} - F_{out} \times S(t)/V(t) \qquad \text{Equation 5}$$

This is a standard form of ordinary differential equation (ODE) of type $$dS/dt + pS = q \qquad \text{Equation 7}$$

The solution to this ODE is:

$$S(t) = \frac{\int \mu(t)q(t)dt + C}{\mu(t)} \text{ where } \mu(t) = e^{\int p(t)dt} \qquad \text{Equation 8}$$

Therefore, we can solve for the concentration of salt, S(t), in the tank at any time, t, given the initial conditions and flow rates. The point of the above example is simply give insight into how one utilizes standard differential equations to solve this type of problem. Now the discussion will turn to the system and mathematics that describe in detail certain embodiments described here.

Figure 3:
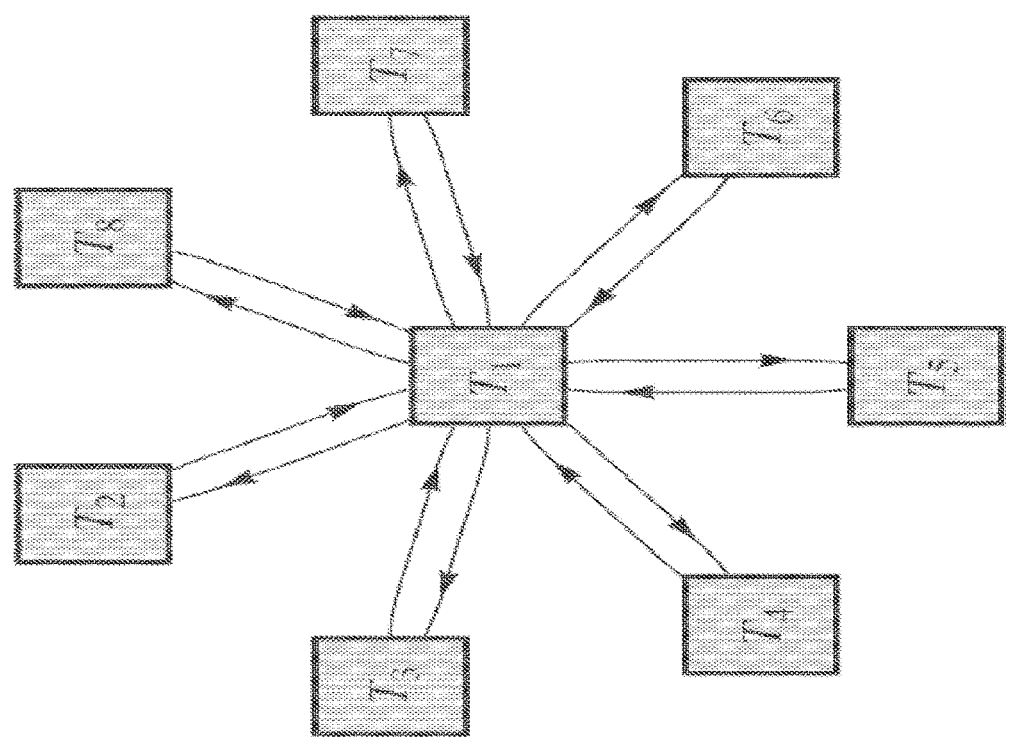
FIG. 3. A mathematical abstraction of a "star architecture" for multi-tank mixing FIG. 4. Two additional bi-directional mathematical models of tank arrangements for potential mixing systems FIG. 5 Two uni-directional mathematical models of tank arrangements for potential mixing systems FIG. 6. Two slave (or satellite) vessels connected to a master vessel with pumps and aseptic connectors. This figure shows the basic configuration for multiple tanks used in a scale-up or expansion process FIG. 7. This figure shows a typical animal cell growth process divided into phases. It also depicts the doubling time.

The term "vessel" will be used as a generic term describing a liquid container which can mean either a tank or a bioreactor. Tanks will be passive or mixing containers while bioreactors will be vessels with the potential to actively control parameters of interest for bio-processing. Consider the arrangement shown in FIG. 3 taken from Mixing Problems with Many Tanks, A. Slavik, Mathematical Association of America, p.806, 2013 (incorporated herein by reference in its entirety). This figure shows an arrangement of tanks in what is referred to as a "star configuration," which has a central vessel and three or more other vessels directly fluidically connected to the central vessel. The star configuration is one possible configuration, but in no way the only configuration that allows for mixing between vessels. In FIG. 3, the tanks are labeled as $T_1 \ldots T_8$. This coupled system is one arrangement that more realistically depicts how tanks or bioreactors can be networked for scalability. If one solves rigorously and unambiguously for flows of mixtures of a substance (e.g., salt) flowing between coupled tanks, one can also solve rigorously for the mixtures of cells and/or media (general supernatant) moving in between bioreactors. This means that one can also create models to predict what flow rates from initial conditions will result in a stationary and homogenous solution. Many of the cases of interest have been summarized in the aforementioned paper. The paper provides a general set of equations which describe the problem of mixing in multiple coupled tanks and allow for solutions. These equations are the general extension of the single tank mixing problem we introduced above. Salt is specifically used in Slavik's paper, but any uniformly mixed substance can be substituted for salt. Equations 9 and 10 below from Slavik use slightly different notation from our simplified example:

$$\frac{dx_1(t)}{dt} = -(n-1)f\frac{x_1(t)}{V} + \sum_{i=2}^{n} f\frac{x_i(t)}{V} \quad \text{Equation 9}$$

$$\frac{dx_i(t)}{dt} = f\frac{x_1(t)}{V} - f\frac{x_i(t)}{V} \text{ for } 2 \le i \le n \quad \text{Equation 10}$$

V is the volume
$T_1$ the central tank is labeled as tank 1
$T_2 \ldots T_n$ are the (n–1) tanks connected to tank 1
$x_i(t)$ is the amount of salt in tank I, ($T_i$), at any given time t Equation 9 describes the change in amount of the additive (salt) as a function of time in the central tank (tank 1), while equation 10 describes the change in salt concentration as a function of time in any tank $T_i$ that is not the central tank. For a given set of initial conditions, the amount of salt in each tank at "time 0" can be solved and the details are worked out Slavik's paper. As mentioned previously, since the mathematical solutions for any mixture can be solved, this solution will also accurately describe the contents of a bioreactor.

Considering the star configuration in FIG. 3 further, it can be seen that N vessels (e.g., eight or even more) can be coupled, where N is only limited by practical considerations (geometrical and space issue, distances, cost). As FIG. 3 is a mathematical idealization of the physical problem, many considerations for applying the aforementioned mathematical machinery to bioreactors has not been specifically addressed.

Figure 4:
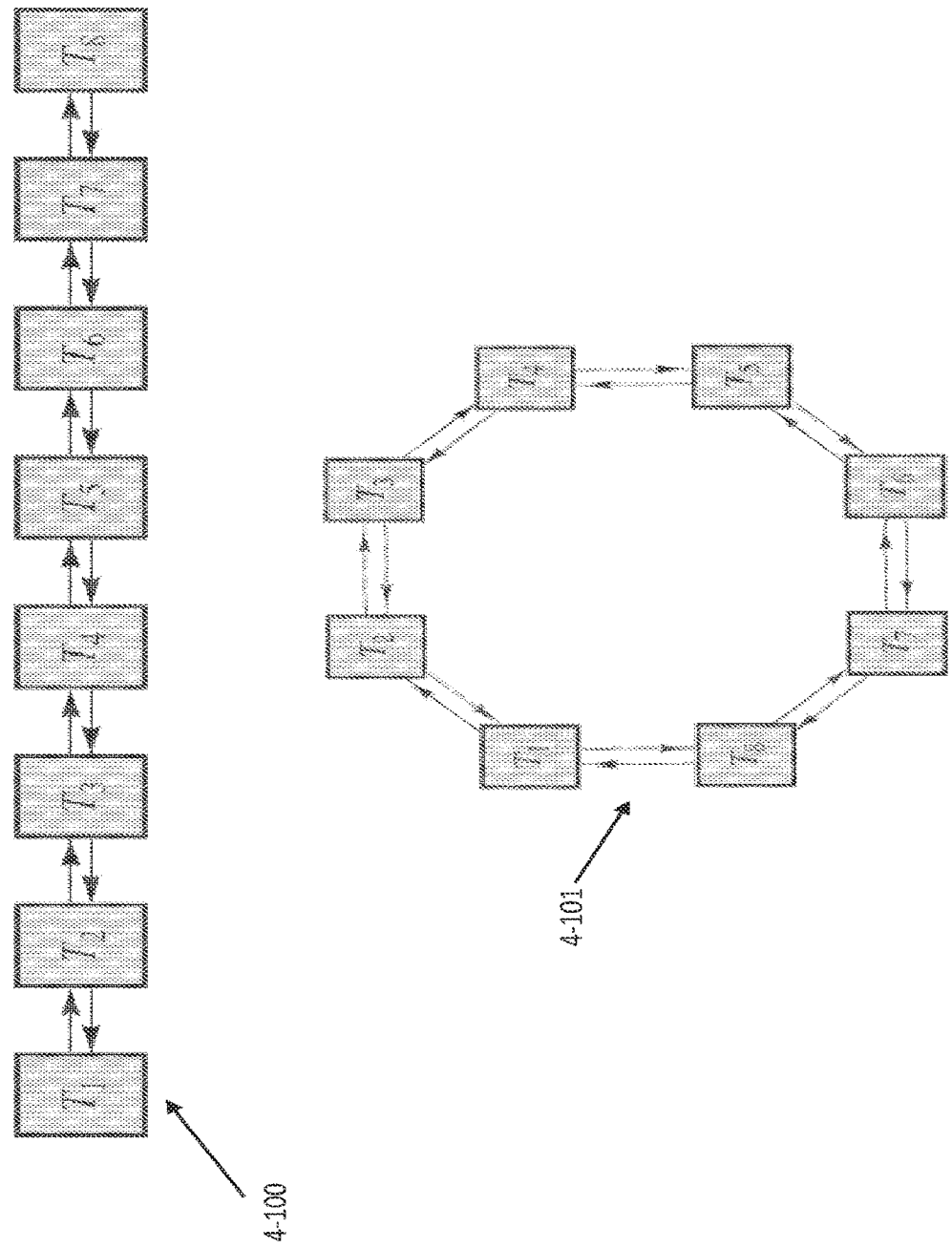

FIG. 4 shows two more mathematical representations of tank arrangements that can used for mixing. Reference numeral 4-100 is a linear chain with fluid moving bi-directionally in-between each tank, while 4-101 is a ring configuration that also employs bidirectional mixing. Note that for well characterized vessels that have been designed with appropriate scale-up/scale-down consistency in their operating parameters, any of these configurations could also contain vessels of different sizes.

Figure 5:
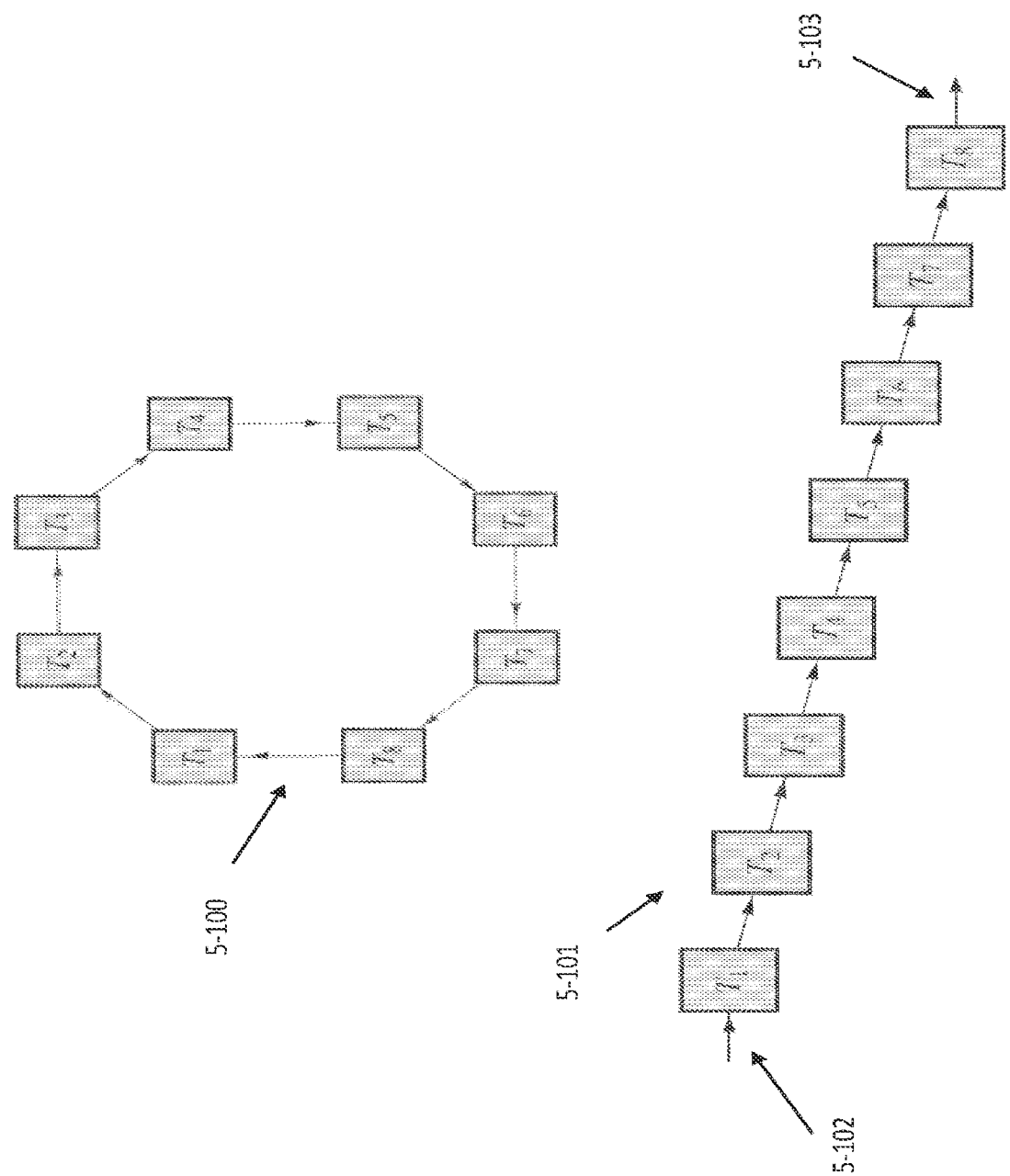

Bidirectional flow between vessels should increase the speed with which the vessels reach equilibrium, but if real mixing can be ensured this directionality is not strictly necessary. This has also been mathematically modelled and two such unidirectional configurations are shown in FIG. 5. Reference numeral 5-100 is the unidirectional analog of the ring 4-100 shown in FIG. 4, while 5-101 is the unidirectional analog of the chain 4-101. Reference numeral 5-102 is the inlet and 5-103 is the outlet which will need to be tied together in a fluid conservative system.

Figure 6:
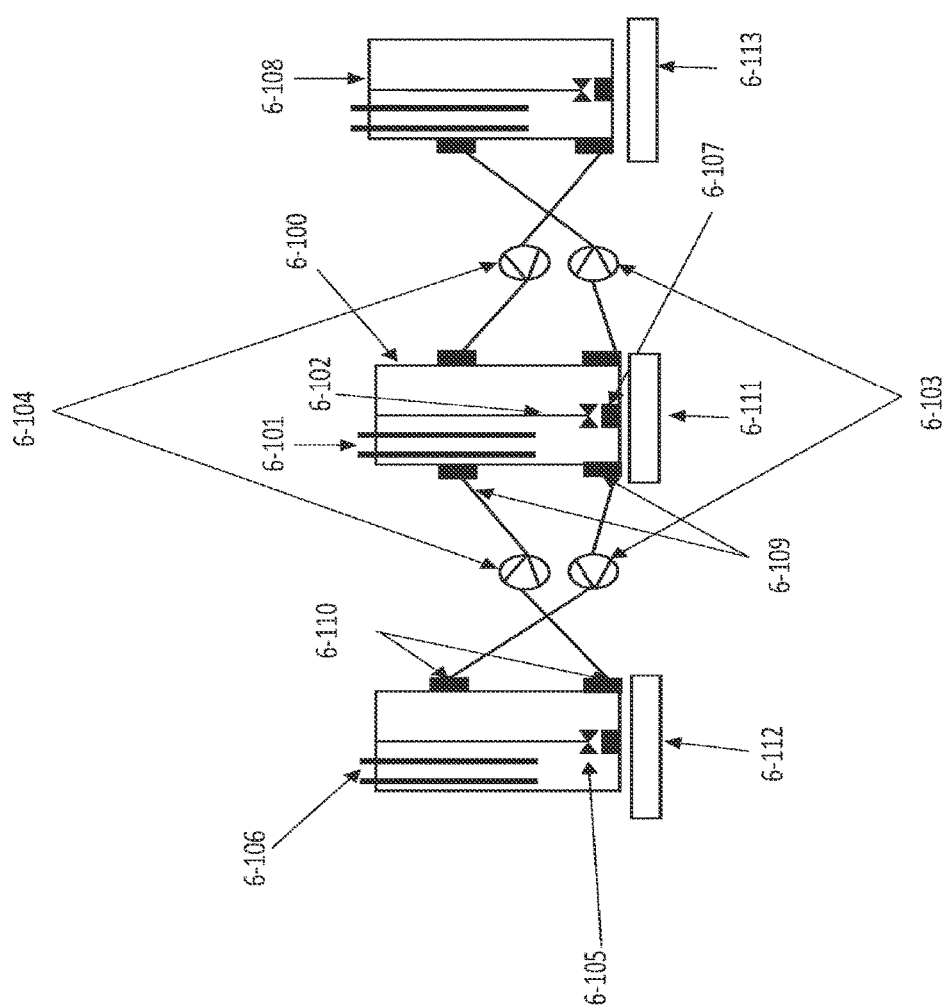

FIG. 6 presents a further example. As shown there, the central bioreactor 6-100 acts as the "master" or controlling bioreactor, while expansion or satellite bioreactors 6-106 and 6-108 are the "slave" bioreactors. As shown, a central bioreactor 6-100 is outfitted with sensors used for control of various analytes or physical levels including but not limited to sensors for: dissolved oxygen, pH, temperature, $CO_2$, cell density, conductivity, and cell viability. The master bioreactor is also equipped with a mixing system and impeller 6-102, and spargers 6-107 to control the dissolved oxygen level or strip $CO_2$. These features are typically used with a control loop (e.g., PID loop) to maintain optimal levels of any of the aforementioned quantities. The control in FIG. 6 occurs though measurements in the master bioreactor, while a slave system is used for monitoring and feedback to both the master loops and the pumps 6-103 and 6-104. In certain embodiments such as those depicted in FIG. 4, the capacity of the bioreactor can be expanded or scaled by attaching other bioreactors such as bioreactors 6-106 and 6-108 to the central bioreactor 6-100. The bioreactors, all typically pre-sterilized, are connected using single-use aseptic connectors and associated tubing sets or other fluidic connectors 6-109 and 6-110 on the master and slave bioreactors respectively. The connectors are shown on both the master and slave but only one set is strictly necessary. These single-use aseptic connectors are now common in the single-use bioprocessing arena and are made by companies such as Pall, GE, and Colder (e.g., pall.com/main/biopharmaceuticals/product.page?id=34125, gelifesciences.com/web app/wcs/stores/servlet/productById/en/GELifeSciences-us/28936612).

Also note that the slave bioreactors may be passive vessels or vessels having structure (e.g., plate or micro-carrier aggregate) for adherent cells where an agitation mechanism is not possible.

The ability to transfer the contents of the master bioreactor to the slave bioreactor is enabled by pumps 6-103 which are shown removing the liquid from the bottom of the bioreactor for hydrostatic pressure considerations. The pumps 6-104 are shown bringing the contents of the slave bioreactor from the bottoms of these vessels back to the master bioreactor. The pumps can be peristaltic pumps or any other known mechanism for moving fluid from one location to another through an enclosed path. Minimal damage to the cells is currently expected when the pumps utilized are low shear centrifugal pumps (e.g., Levitronix pumps, levitronix.com) but this also not strictly necessary and will depend on the speed of transfer required and the robustness of the cell line in use. In some embodiments, the bioreactors are disposed on scales or load cells 6-111, 6-112, 6-113 in order to maintain equal mass/volumes in each vessel. If the total volume is known in advance it is possible to have only a subset of the bioreactors on scales by using a simple algorithm incorporating the requisite addition or subtraction of the volumes using mass balance.

It should be noted that by connecting bioreactors of known scalability (parameters uniform enough for successful scale-up) the issue of scale-up as discussed earlier has been circumvented. In various implementations, the pumps force exchange of contents between the bioreactors quickly enough that for all intents and purposes the system can be considered one bioreactor. Quickly enough means that all of the bioreactors are uniform in terms of certain parameters of groups of parameters and that a sample from one of the bioreactors cannot be distinguished from a sample taken from another at the same time. Any of the parameters described above can provide the measure of uniformity; such parameters generally relate to fluid dynamic parameters (e.g., shear experienced by cells, Reynolds number), composition parameters (e.g., concentrations of dissolved components and/or pH), and mass transfer parameters (e.g., oxygen transfer coefficient). Though each cell line and process is different, if the exchange rate between the vessels exceeds the rate at which such parameters change (and, e.g., cell growth (doubling) rates) the requisite uniformity is preserved. This can be proven experimentally for each cell line and process and controlled rigorously after this by adjusting the pump speeds accordingly and/or by monitoring the key process sensors. The sensors can be utilized as a feedback mechanism for the pump speed to maintain homogeneity within the typical error (or dead-band) of the associated control loop.

Figure 7:
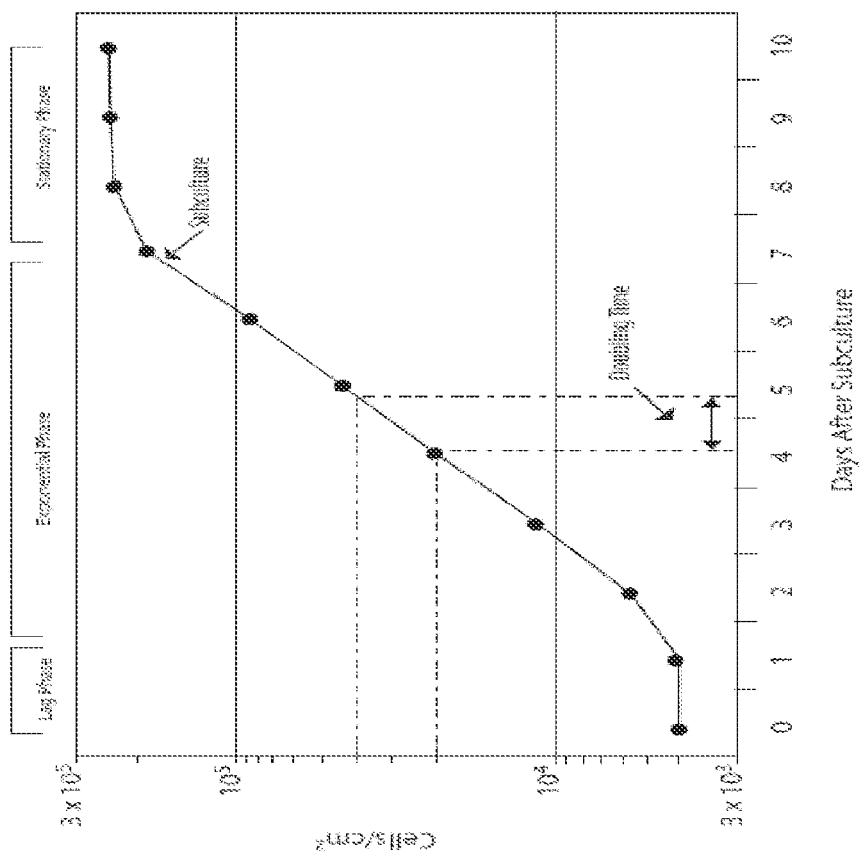

It will be helpful to review here the cell growth process in terms of the disclosed embodiments. Specifically, how do cell populations grow and change as a function of time? A typical cell growth curve is shown in FIG. 7. As shown in the figure, there is a lag phase immediately after seeding of the vessel where the cells are said to be recovering from the stress of being immersed in new media. Next is the log or exponential phase where the growth rates accelerate until the media is exhausted or other detrimental effect occurs. This is followed by the stationary phase and the decline phase. One measure of the cell growth rate is the "doubling time" or the time it takes for the cell population to double in population (—see, ATCC Animal Cell Guide) during the "log" phase of the growth cycle. The doubling time for the cell lines under the growth conditions is typically well characterized. For example, a typical CHO (Chinese hamster ovary) cell line has a doubling time of >15 hours, while human cardiac cells and mesenchymal stem cells from mice have median doubling times of approximately 29 and 22 hours respectively. Microbial cell doubling times are much faster; *Escherichia coli* have a doubling time on the order of 15-30 minutes. The doubling time can provide a reasonable measure of the rate of change of the growth process and there serve as a benchmark for the rate at which material needs to be exchanged between vessels in order to maintain homogeneity of the cell population. In the lag, stationary, and decline phases, the rate of exchange required for homogeneity will be reduced from the exponential growth phase where the cell doubling rate is the fastest. During the lag phase where the cells are doubling very slowly, the exchange rate can be commensurately slow. If a slave vessel is added during the log phase, a starting point for achieving homogeneity can use the volumetric flow/exchange rate (pump rates in and out of the vessels) benchmarked against the cell doubling time as a metric. The question of the required rate of volumetric exchange can be reduced to the question of how many times does the volume of the vessel need to be exchanged compared to the doubling time. If the vessel contents are exchanged at least an order of magnitude faster than the doubling time, the multiple vessel contents will almost certainly be homogeneous. How much slower can the rate of exchange of vessel contents be before homogeneity is lost will depend on the specifics of the cell line and the process?

As an example, if a CHO cell growth process were started in a 100 L working volume bioreactor with a 4:1 turndown ratio completely filled with media and cells and the process was in the lag phase, the group running the process might require that a second identical and perhaps third identical bioreactor are attached as slave vessels in order to meet their product and/or titer goals. In this scenario to set up the system, the outgoing pumps from the master would turn on such that the second and third bioreactors are filled with >25 L with the volumes being determined by change in measured values on the load cells. As long as the cells and supernatant are transferred in a time period such that there is little change in the cell population (e.g.: the cell population can still be considered to be firmly in the lag phase), the master and slaves can still be treated as homogenous or uniform. The return pumps (from slave vessels to the master vessel) would remain off until the desired volume was reached in the slaves and then active bi-directional exchange between the vessels would commence. Additional media can be slowly added to the master or to multiple vessels again based on the total required volume and/or yield for the process; the master and slaves can all eventually be filled to the working volume. The rate at which the media is introduced into the system might have to correspond to the rate of change of cell density so that the cells are not substantially perturbed. During the lag phase, as mentioned before, the cells are not growing rapidly and therefore the exchange rate volumetric flow requirements are low. In the log phase, if the doubling time is 15 hours, a starting point based on the above discussion is to exchange the vessel volume every 1.5 hours. This means that 100 L/90 minutes or about 1.1 SLPM for the volumetric transfer rate. Based on measurements of relevant cell growth parameters including but not limited to the bioreactor pH, metabolite concentration, cell density, cell viability, etc. the volumetric exchange rates can be reduced. In certain embodiments, different processes use different algorithms to control the volumetric exchange rates and therefore maintain homogeneity. In certain embodiments, simply maintaining a very high volumetric exchange rate (compared to the fastest doubling time) throughout the entire growth process would simplify the system and uncertainty about homogeneity.

As mentioned, in certain embodiments, the master vessel will generally control the important quantities such as dissolved oxygen, pH, and temperature. But in certain embodiments there can also be actuators in the slave vessels as shown in FIG. 6, reference numerals 6-106 and 6-108. Some control architectures depend on the physical embodiment of the system. For example, if the exchange rate between the vessels is fast compared to a thermal time scale of any one vessel, in some implementations, there is not only no need to control temperature in each individual vessel there is also no need for an actuator (e.g., heating blanket) that is set at a nominal value. Having a single master control loop avoids "pulling" or communication between control loops and simplifies the control scheme. Having actuators and sensors in the slave bioreactors as well allows the control to be performed through the master and allows the speed of the pumps to equilibrate the master and slave bioreactors; the sensors in the slave bioreactors compared to the sensors in the master allow a feedback path for the control of the pumps if desired. For example, having impellers, sensors, and spargers in the slave bioreactors controlled, but having the sparging and mixing in the slave vessels controlled by the master is a suitable control scheme. Passive control by design is also possible, where the speed of the pumps allows the slave vessels to be essentially passive elements or tanks.

Figure 8:
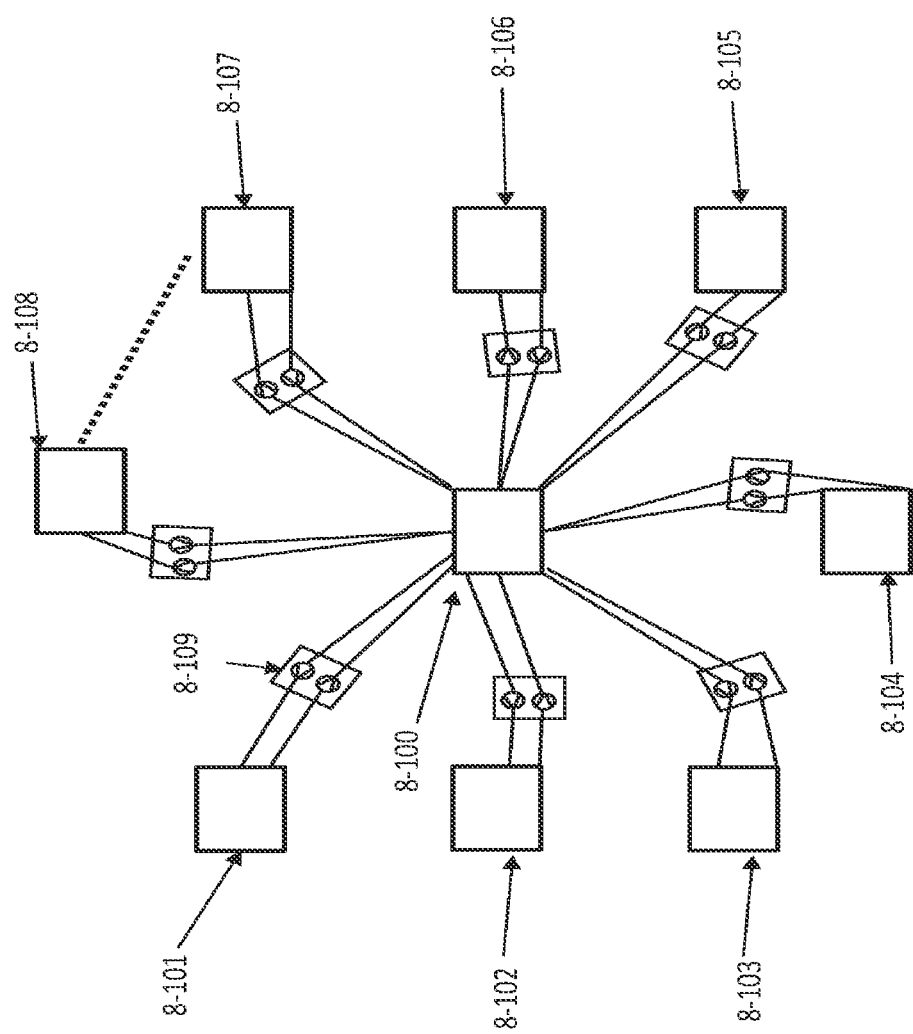
FIG. 8. This figure shows a physical representation of the star architecture for n vessel expansion FIG. 9. A multi-tank expansion system equipped to provide modalities for personalized medicine applications

FIG. 8 extends this concept of scale-up by multiple connected vessels and may fully utilize the mathematics described in equations 9 and 10. In FIG. 8, reference numeral 8-100 shows a simplified version of the master bioreactor where the spargers, sensors, impellers etc. are not shown but can be considered as included. The pumps (bidirectional) are shown as a unit 8-109, and for the sake of clarity in FIG. 8 the bioreactors 8-101 through 8-107 are shown in simplified form and without showing the aseptic connectors, while a bioreactor 8-108 block illustrates the extension to any number of vessels. This limit is set by physical factors, cost, and practical considerations—not by theoretical extension or mathematics. If scaling the system (pumps, connectors, etc.) becomes cost prohibitive, this scaling by discrete addition of tanks can be used in conjunction with a conventional scale-up process to limit the number of tanks required. For example, if a bioreactor with a 5:1 turndown ratio is used, one can start the process in say a 30 L bioreactor turned down to 6 L, and then fill it to 30 L. After this a second or third bioreactor can be added which takes the total working volume to 100 L. The production can then move to the 650 L vessel which can be turned down to approximately 115 L, yet is expandable with two additional vessels to 1950 L. The largest single-use bioreactor in commercial production today is 2000 L, and a large number of bioreactor volumes in between are required to scale to this volume which means more parts, more scaling, more effort, and more cost. The example just reviewed allows scaling from 6 L to almost 2000 L with only one scale-up step in terms of bioreactor maximum working volume.

Another application for this type of scalable system is in the personalized medicine arena. This area of application includes but is not limited to stem cell therapies, chimeric antigen receptor T Cells (CAR-T) therapies, and tumor infiltrating lymphocyte (TIL) based treatments where small but potentially expandable volumes are required. Currently for CAR-T type therapies a typical batch size is on the order of 1 L, and the US Food and Drug Administration (FDA) requires approximately one-half of this quality and safety testing. In such immune-oncology applications, the starting volume of cells collected and selected from a patient sample is very small (30 mL) compared to the required batch size (3 L) and represents a 100× amplification at high cell density in a single-patient dose scenario. The amplification challenge is even greater for heterologous treatments where a batch size of 300 L is targeted (10,000 amplification), if the treatments costs are to be affordable and quality assurance is to be amortized over a few thousand doses. The disclosed embodiments provide a useful mode of meeting such challenges.

In personalized medicine applications, if the batch is lost a patient can lose an opportunity for live saving treatment at the last stages of his or her illness. Batches often fail owing to contamination of the process. Therefore, the ability to expand a 30 mL sample in a linear progression of effectively identical bioreactors is very appealing as the process can start in one 300 mL vessel, and be scaled to two and eventually three or more vessels simultaneously as the cells grow. Once the process is scaled into three or more vessels, the contents of one vessel can be removed for storage in case of a contamination of the whole batch, analyzed for quality/ or stored as a treatment dose in cold storage. The two vessels can then be scaled back into the empty vessel and a second vessel volume removed at that point. This process can be repeated as necessary with a batch collected every week, for example, without compromising the viability of the cell culture as a vessel can be drained and refilled with media or detached and a new vessel aseptically attached (or all vessels in the train can be attached at the start with some vessels being empty and a sterile valve being used to determine when and if they are added to the process chain). This can then be viewed as a continuous fed-batch process which supports discrete volume changes. Batches can also be pooled into a single dose as they can be shown to be identical material.

In the case of very shear sensitive cells, the satellite vessel concept in this disclosure can be applied with a set of master vessels having impellers and full sensor analytics being utilized to control the oxygen, pH and metabolite concentrations of the media, and the satellite vessel(s) being passive with either a packed bed of micro-carriers, hollow fibers or adhesion plates. With the pumps, such as in FIG. 9, connecting the passive vessels to the master vessels, any viruses or bacteria can be isolated to a single vessel by the addition of appropriate filters 8-119 (typically <0.22 μm for viruses) in the lines between the vessels. The volume of the original cell sample would be divided among the satellites thereby de-risking the entire sample from failure to expand.

Figure 9:
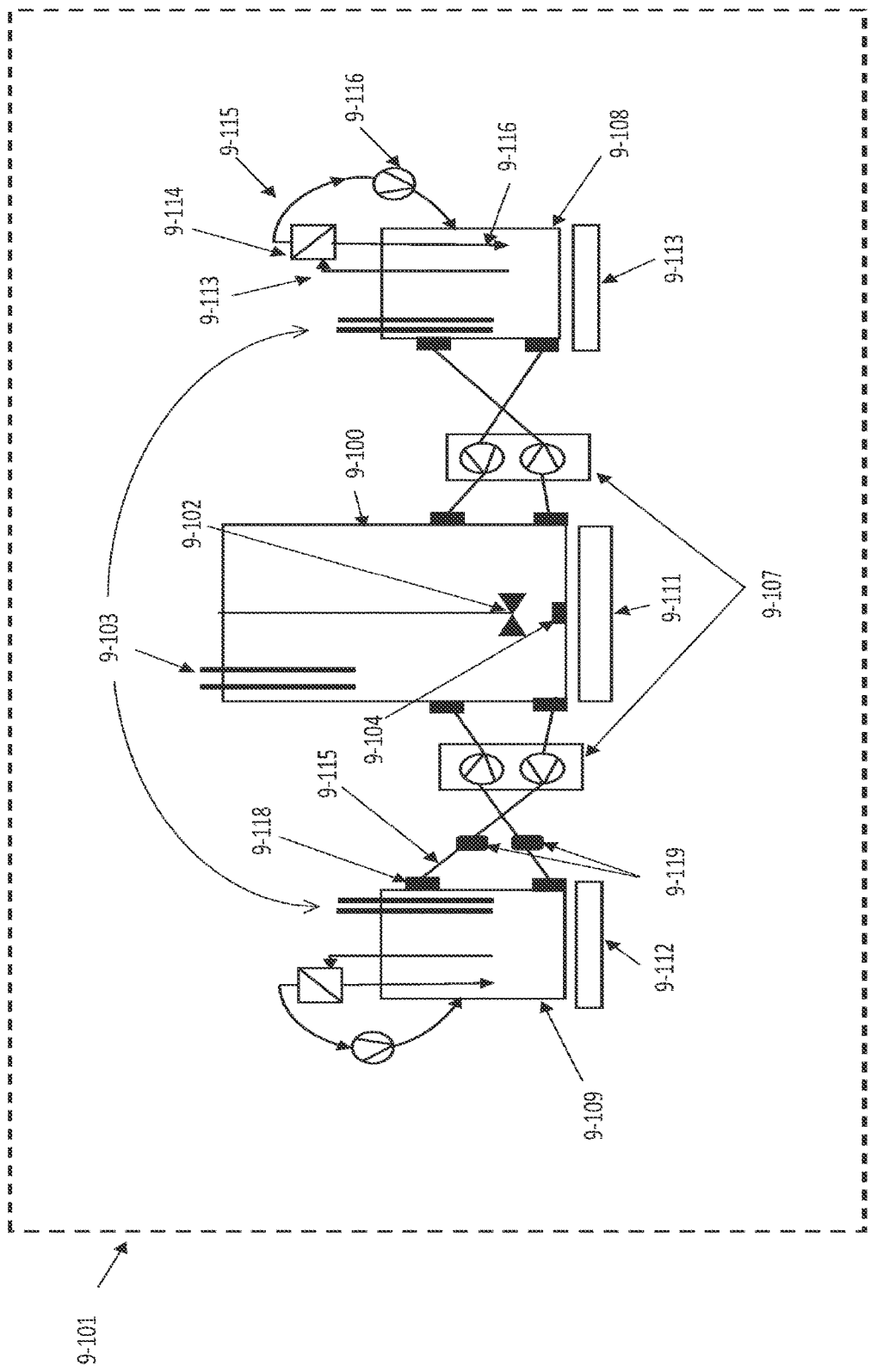

FIG. 9 shows a system of three networked vessels, though it is expandable to N vessels as well. A main bioreactor 9-100 networked to satellite/slave vessels 9-108 and 9-109 with aseptic connectors 9-118, bi-directional pumps 9-107, in line virus filtration 9-119, along with aseptic connectorized tubing sets 9-115 which are both called out specifically only on one vessel, 9-109, but shown on all three vessels. The main bioreactor, or master, 9-100 is shown with an impeller 9-102 and sparger 9-104. These features are not explicitly shown on the slave vessels 9-108 and 9-109 as they may not be required. In this embodiment, if the cells are sensitive to shear and/or for lower cost, the vessels can have the mixing, oxygenation and pH adjust all take place in the master tank. Given this possibility, the master tank here is shown as larger in size and volume than either of the slave tanks so that it can also act as both ballast and a reservoir for the oxygenated, pH adjusted media. Sensors 9-103 are shown in all three vessels so that there is feedback for monitoring and control purposes. Specifically, either changing the pumps speeds or changes to the analyte values in the master bioreactor.

Additionally, in FIG. 9, the slave bioreactors are shown being utilized in perfusion mode or a cell separation mode depending on the application. A tube 9-113 which allows the contents of the bioreactor to be brought up to the cell retention/separation device (acoustic separator, filter etc. (e.g.: applikon-bio.com/en/news2/itemlist/category/52-biosep, spectrumlabs.com/filtration/KR2System.html), 9-114 is shown with a return loop 9-115 to the bioreactor with a pump, 9-116, or other device to move the fluid in the required path. The vessels can therefore be used to implement a perfusion process with actual growth process occurring in the slave vessels, and oxygenation and control residing in the master vessel, or in a cell expansion mode with a similar division of tasks. The cell expansion mode is of interest as T-Cell, stem cell expansion, or adherent cell growth can occur in the slaves without a need for an impeller and without the accompanying shear. The vessels are again shown on scales or load cells 9-111, 9-112, 9-113 for mass/volume balancing between the vessels. Finally, the entire system can be enclosed in an incubator or incubator shaker 9-101 for temperature control, as well as mixing if none of the vessels were equipped with impellers (e.g., shake flasks or bioreactors specifically designed to work without an impeller kuhner.com/en/product/shakers/singleuse/sb200-x.html). This can further reduce the per-use cost of the vessels.

As indicated, a multi-vessel bioreactor system includes two, three, or more fluidically coupled vessels configured to collectively carry out a bioreaction. They do so by maintaining nominally uniform or consistent conditions between the vessels during the bioreaction. As a consequence, the vessels share reactants and products between the vessels during the bioreaction. This may be accomplished by including fluidic paths (sometimes implemented herein as fluidic connectors, e.g., tubes) coupling the vessels to one another during the bioreaction and fluid transfer devices (pumps) in at least some of the one or more fluidic paths or connectors.

Typically, the bioreactor system also includes a control system configured to control reaction conditions in the vessels to carry out the bioreaction. Among other responsibilities, the control system may be tasked with maintaining uniform process conditions between the vessels during the bioreaction. To this end, the control system may be configured to (i) read or receive values of at least one parameter characterizing a culture medium or other reaction fluid in one or more of the vessels during the bioreaction, (ii) use the values to determine an adjusted flow rate in at least one of the fluidic connectors to maintain substantially uniform values of the parameter in the reaction fluid from vessel-to-vessel among the vessels, and (iii) control at least one of the fluid transfer devices to adjust the flow rate determined in (ii). By controlling the flow of reaction fluid in this manner, the temperature, pH, selected analyte concentrations (e.g., dissolved oxygen concentration, glucose concentration), hydrodynamic conditions, etc. can be maintained substantially consistent or uniform across the vessels. Substantially consistent or uniform is determined from perspectives relative to the bioreaction, so, for example, the cell viability, cell productivity, titer, etc. are consistent from vessel-to-vessel. Magnitude differences within which a process condition is still consistent are determined in various ways, as appropriate, for performance of the bioreaction. For example, it may be appropriate for the mass concentration of a selected analyte or product to deviate by no more than about 5% from one vessel to another, or for pH to vary in magnitude by no more than about 0.2 pH units from one vessel to another, for temperature to vary by no more than about 0.5 degrees C. from one vessel to another. Again, the main point is that the variability is within bounds that produce consistent bioreaction results from vessel-to-vessel. These results may be product titer and/or concentration, cell viability, etc.

In certain embodiments, the control system is configured to (i) read or receive parameter values characterizing the culture medium or other reaction fluid in one or more of the vessels during the bioreaction, and (ii) control the one or more fluid transfer devices to transfer the culture medium between the two or more vessels such that the time required to exchange the culture medium in the vessels is within an order of magnitude of the time required for cells in the vessels to double under conditions in the vessels. For example, the time required to exchange the culture medium in the vessels may be at most about one-half the time required for cells in the vessels to double under conditions in the vessels. Under more stringent operating conditions, the control system will direct transfer for the culture medium faster, such that the time required to exchange the culture medium in the vessels is at most about one-third, or one-fifth, or one-tenth (or even one-twentieth) the time required for cells in the vessels to double under conditions in the vessels. The actual rate will depend in part on the current conditions in the bioreactor system and degree of uniformity needed (e.g., the pH should not vary by more than about 0.1 pH unit from vessel-to-vessel). Note that the time required to exchange culture medium in a vessel or vessels is based on the amount of culture medium currently in the vessel(s), which is not necessarily the working volume of the vessel(s). (In practice, of course, the system would not remove all the culture medium from a vessel during the exchange; the system would flow in new medium and at the same time push out a corresponding amount of old medium.) Further, the cell doubling time varies depending up a number of factors including the cells' current growth phase, and where in the phase most of the cells currently reside. For example, the doubling time is dramatically different for cells in the lag phase and cells in the log/exponential phase. See the discussion of FIG. 7.

In certain embodiments, the control system drives flow rates of the culture medium into each of the vessels such that the time require to exchange culture medium in any of the vessels is shorter than the mixing time of the culture medium for the respective vessels. In certain embodiments, the exchange time is within an order of magnitude of the mixing time. For example, the exchange time may be no greater than about one-half the mixing time, or no greater than about one-third, or one-fifth, or one-tenth of the mixing time. In certain embodiments, the exchange time is no greater than about one-tenth the mixing time. One way to consider this is that the time required fully exchange culture medium present in a vessel using the operating flow rate into the vessel is faster than the time required to mix the components of the vessel using the intrinsic mixing drivers of a vessel (e.g., convection, diffusion, etc.). As explained, mixing time may be defined in various ways. For purposes of this embodiment, is assumed that the mixing rate is defined by the time it takes for a recently introduced tracer to be homogeneously distributed within the bioreactor to the level required for a successful bioprocess. This assumes that culture medium is not entering or leaving the vessel during the mixing; i.e., it assumes that the vessel where the mixing occurs is a closed system. In certain embodiments, homogeneous distribution is defined such that the concentration of tracer varies by no more than about 10% between any two points in the vessel.

Vessel

As should be apparent, there are many benefits in using relatively small vessels. Examples of such benefits include avoiding certain scale up challenges (e.g., less experimentation and uncertainty), reducing intra-vessel variation in process conditions, etc. Therefore, the sizes of the individual vessels in the multi-vessel bioreactor system are relatively small. As an example, each vessel has a working volume of not greater than about 700 liters, or not greater than about 500 liters, or not greater than about 100 liters, or not greater than about 50 liters. It should be understood that the terms "total volume" and "working volume" are sometimes used in the industry, and consistent with that use, the term total volume refers to a vessel's total capacity, regardless of limits of fluid volume, while the term working volume refers to the maximum volume of fluid that can be filled in a vessel for undergoing a bioreaction.

As indicated, a bioreactor system may include two, three, or more vessels. The numbers of vessels influences, but does not completely dictate, the ratio of total working volume of the bioreactor system (e.g., the sum of the working volumes of the two or more vessels making up bioreactor system) to the working volume of largest of the two or more vessels. In certain embodiments, that ratio is at least about 2 or at least about 3. Ratios in the range of about 2-4 are often appropriate for relatively large total volume bioreactors systems; e.g., systems having a total volume of about 1000 liters or greater, or about 1500 liters or greater, or about 2000 liters or greater. For some applications, such as smaller scale applications (e.g., about 500 liters total working volume or less) or personalized medicine applications, the ratio of total working volume of the bioreactor system to the working volume of largest of the vessels may be a larger, e.g., at least about 6. The total number of vessels employed in the bioreactor at any given time during the bioreaction may be at least about 5, at least about 6, at least about 10, or at least about 12. The number is chosen based on a number of factors including the bioreactor product or application, the total working volume of the bioreactor system, the need to replace, remove, or add vessels over the course of a bioreaction, etc.

As an example of the power of this approach when coupled with typical vessel turn down ratios, consider a 4:1 or 5:1 turn down ratio in a 500 liter vessel, the working volume of the coupled multi-vessel system can scale from 100-125 L all the way to 1500 L to 2000 L without changing vessel sizes. This means a manufacturer of bioreactor vessels can have a focused product offering in which only a few vessel sizes are needed to provide an extremely wide range of effective bioreactor volumes. For example, the train of four or more bioreactor sizes in FIG. 1 can be replaced with two or three total bioreactors for the entire scale up process.

In some implementations, the individual vessels of the bioreactor system are similar to one another in working volume, geometry, materials of construction, and/or agitation/mixing system. For example, the vessels may have similar turndown ratios; e.g., no two vessels have turndown ratios varying from one another by more within about 20%. In some embodiments, all vessels are made from the same material; e.g., all vessels have polymeric vessel walls or vessels have stainless steel walls.

In certain embodiments, as explained, one of the multiple vessels is a master vessel and the others are satellite or slave vessels. Frequently, though not necessarily, the master vessel has a larger working volume than any of the satellite vessels. Typically, the master vessel is used to provide some measure of control over the conditions in the satellite vessels. For example, the control system may monitor and adjust conditions first in the master vessel and then use inter-vessel fluid transfer have conditions in the satellite vessels follow those in the master. In certain embodiments, the master vessel includes one or more sensors for the pH, temperature, a cell metabolite concentration, and dissolved oxygen in the culture medium. In certain embodiments, the control system receives values of such parameters from sensors on the master and/or satellite vessels and uses these values to first adjust conditions in the master vessel. In certain embodiments, the control system includes a single control loop configured to control the master vessel, and in some cases at least a mixing system configured to agitate the culture medium in the master vessel. In certain embodiments, the satellite vessels contain spargers set at a substantially constant rate. In such cases, sparging air or oxygen can occur in the satellite vessels, while the primary control point employs sensors in the master vessel.

In some cases, the master vessel may include mixing system configured to agitate the culture medium in the master. In some of these cases, none of the satellite vessels includes a mixing system. Examples of suitable mixing systems, whether implemented in a master or satellite vessel, include impellers, orbital shakers, wave rockers, and plungers.

As explained, the arrangement of vessels, as dictated by direct connections between individual vessels in the bioreactor system, may have many configurations. Examples include a star configuration, a linear configuration, closed loop configuration, and a combination of any two more of these. For example, the arrangement may be a spoke a wheel configuration, or a lasso configuration having a closed loop with a tail extending from one of the loop vessels, or a fused ring configuration. The arrangement can be bidirectional fluidic connections or simply a closed loop fluidic connection. As illustrated, a closed loop configuration forms a closed loop for fluid flow.

In certain embodiments, the bioreactor systems includes an additional vessel initially unconnected to the two or more fluidically connected vessels, but it includes a supplemental fluidic connection for connecting to the bioreactor system after the bioreactor system has been operating. This allows the systems to scale up during the course of the bioreaction, as may be appropriate when culturing a patient's own cells (or a modified variant thereof) to be used in a subsequent treatment administered to the patient. In some cases the control system is configured to at least partially fill the additional vessel with culture medium from one or more other vessels during the bioreaction. Alternatively or in addition, one or more of the vessels of the system is configured to be removed, before the bioreaction completes, along with their culture medium and cells grown in the medium.

Control System

As mentioned, the control system may be tasked with maintaining uniform process conditions between the vessels during the bioreaction. This may require that, for example, cell growth rates and/or product titers do not differ by more than a few percent (e.g., no more than about 10%) from vessel-to-vessel.

In various embodiments, the control system is configured to maintain substantially uniform values of pH from vessel-to-vessel. For example, the control system may be configured to adjust conditions in the two or more vessels to ensure that the mean pH of the culture medium in the two or more vessels does not vary from one vessel to another by more than about 0.2 pH units (or by no more than about 0.1 pH units or by no more than about 0.05 pH units). This is particularly useful when the individual vessels are small enough and/or well-mixed enough that the internal variation in conditions is minimal. For example, the two or more vessels and the control system may be designed or configured such that pH of the culture medium within any of the vessels has variance of at most about 0.1 pH units.

In certain embodiments, the control system is further configured to adjust conditions in the two or more vessels to ensure that the mean culture medium temperature is held from vessel-to-vessel to within about 0.5 degree C. (or within about 0.1 degree C.).

In certain embodiments, the control system is further configured to adjust conditions in the two or more vessels to ensure that shear forces experienced by cells in the two or more vessels are substantially equal from one vessel to another during the bioreaction. For example, the number of cells dying due to shear may be within 5% between any two vessels. Ideally, during the course of a bioreaction, few cells in any vessel or die due to shear forces or at least no more than about 10% die due to shear forces."

In certain embodiments, the control system is further configured to adjust conditions in the two or more vessels to ensure that culture medium gas transfer rates in the two or more vessels are substantially equal from one vessel to another during the bioreaction (e.g., the mean values of any one or more of the above-listed transfer parameters do not vary by more than about 5% from vessel-to-vessel). Of course, the dissolved oxygen level should not be below a level at which cells begin dying from lack of oxygen.

In certain embodiments, the one or more of the vessels in the bioreactor system are provided on scales and/or load cells to monitor their masses during the bioreaction. The control system may be configured to monitor outputs from the scales and/or load cells and adjust flow rates between vessels to ensure the volume/mass in the individual vessels remains within specification.

Broadly speaking, the controller may be electronics having various integrated circuits, logic, memory, and/or software that receive instructions, issue instructions, control operation, enable cleaning operations, enable measurements, and the like. The controller hardware may contain one or more processors, memory devices, and interfaces for communicating with sensors, pumps, spargers, mixers, and the like. The processors may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on a bioreactor.

The controller may be integrated with electronics for controlling operation before, during, and after execution of a bioprocess. The controller, depending on the processing requirements and/or the type of system, may be programmed to control any of the processes disclosed herein, including pumping media between vessels, adjusting temperature, controlling media conditions such as pH, nutrient concentration, etc., and removing products of bioreactions.

The controller, in some implementations, may be a part of or coupled to a computer that is integrated with, coupled to the system, otherwise networked to the system, or a combination thereof. For example, the controller may be in the "cloud" or all or a part of a facilities host computer system, which can allow for remote access of the bioprocessing. The computer may enable remote access to the system to monitor current progress of bioprocess operations, examine a history of past bioprocessing operations, examine trends or performance metrics from a plurality of bioprocessing operations, to change parameters of current processing, to set processing steps to follow a current processing, or to start a new process.

In some examples, a remote computer (e.g. a server) can provide process operating instructions to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. Thus as described above, the controller may be distributed, such as by comprising one or more discrete controllers that are networked together and working towards a common purpose, such as the processes and controls described herein. An example of a distributed controller for such purposes would be one or more integrated circuits on a reactor in communication with one or more integrated circuits located remotely (such as at the platform level or as part of a remote computer) that combine to control a process on the reactor.

Each algorithm or other computational element of a controller may be implemented as an organized collection of computer data and instructions. In certain embodiments, a module for controlling flow between vessels, a module for adjusting temperature of one or more vessels, a module for adjusting introduction and/or removal of material from one or more vessels can each be viewed as a form of application software that interfaces with a user and with system software. System software typically interfaces with computer hardware, typically implemented as one or more processors (e.g., CPUs or ASICs as described) and associated memory. In certain embodiments, the system software includes operating system software and/or firmware, as well as any middleware and drivers installed in the system. The system software provides basic non-task-specific functions of the computer. In contrast, the modules and other application software are used to accomplish specific tasks. Each native instruction for a module is stored in a memory device and is represented by a numeric value.

At one level a computational element is implemented as a set of commands prepared by the programmer/developer. However, the module software that can be executed by the computer hardware is executable code committed to memory using "machine codes" selected from the specific machine language instruction set, or "native instructions," designed into the hardware processor. The machine language instruction set, or native instruction set, is known to, and essentially built into, the hardware processor(s). This is the "language" by which the system and application software communicates with the hardware processors. Each native instruction is a discrete code that is recognized by the processing architecture and that can specify particular registers for arithmetic, addressing, or control functions; particular memory locations or offsets; and particular addressing modes used to interpret operands. More complex operations are built up by combining these simple native instructions, which are executed sequentially, or as otherwise directed by control flow instructions.

The inter-relationship between the executable software instructions and the hardware processor is structural. In other words, the instructions per se are a series of symbols or numeric values. They do not intrinsically convey any information. It is the processor, which by design was preconfigured to interpret the symbols/numeric values, which imparts meaning to the instructions.

Fluidic Connections and Fluid Transfer Devices

As mentioned, one or more fluidic connectors, or more generally fluidic paths, connect the vessels. In general, the connectors are configured to provide flow of culture medium between the two or more vessels during the bioreaction. They may be pipes, tubes, weirs, and the like. They have a fluid travel length, cross-sectional diameter, surface roughness condition, rigidity/flexibility, etc. as necessary to support the flow rates and flow conditions (e.g., laminar, turbulent, transitional) for transferring culture medium or other reaction fluid to maintain the required level(s) of uniformity from vessel-to-vessel. In certain embodiments, the fluidic paths are made from material that is USP Class VI/ISO10993, animal component derived free, latex free, phthalate free, and/or gamma/beta radiation stable.

In some implementations each of the fluidic connectors is configured to permit bidirectional flow of the culture medium between two of the vessels. In such cases, two or more flow paths may be provided between vessels or a two-way pump may be provided in a fluidic connector.

Various physical structures of the fluidic connectors may be employed. One example includes tubing and aseptic connectors attached to the two or more vessels. In some implementations, at least one fluid path of the fluidic connectors attach at or near to bottoms of the two or more vessels. This allows the fluid flow to take advantage of hydrostatic pressure head, particularly in large vessels. Of course, other vessel designs may suggest the locations of the inlet and outlet fluid paths. For example, in the case of a two way fluidic connector and a vessel having an impeller directing fluid downward, the outlet of fluidic connector may attach below the bottom level of the impeller, and the inlet fluidic connector may attach at or above the top level of the impeller.

Various types of fluid transfer devices may be employed. For example, at least one of the fluid transfer devices may be a pump. A pump is broadly defined to include all types used to move liquid by mechanical action. Examples include rotodynamic pumps (e.g., centrifugal or axial) and positive displacement pumps (e.g., a syringe type, a gear type, diaphragm type, a piston type, a plunger type, a screw type, or vane type).

Perfusion

As explained, one or more vessels of the bioreactor system may be configured to operate in a perfusion mode, whereby culture medium is distributed (flows) over the cells constrained to the vessel. Typically, in perfusion mode, conditions are maintained such that cells are retained in a vessel while fresh media is brought in. The rate that the media is brought in depends on the cell line and the phase of growth. A goal is to maintain a substantially optimal growth environment (in terms of nutrient concentrations, product titer, temperature, hydrodynamic conditions, etc.), and, as a consequence, the cells in a vessel maintain a relatively consistent biological state in terms of production rate, viability, etc. for a longer period of time compared to batch mode or fed batch modes of growth. In certain embodiments, a bioreactor system configured to operate in perfusion mode includes two or more fluidically coupled vessels configured to collectively carry out a bioreaction, where at least one of the vessels is a perfusion vessel having a fluidic inlet, a fluidic outlet, and a filter or other mechanism configured to prevent biological cells from leaving the perfusion vessel during the bioreaction. Additionally, as with some other systems described herein, a perfusion mode bioreactor system may include one or more fluidic connectors (or more generally fluidic paths) coupling the two or more vessels to one another and, during the bioreaction. The system typically includes one or more fluid transfer devices (e.g., pumps) in at least one of the one or more fluidic connectors. Collectively, the fluidic connectors and the fluid transfer devices are configured to provide flow of culture medium between the two or more vessels.

Still further a perfusion mode bioreactor system may contain a control system configured to (i) read or receive values of two or more parameters characterizing the culture medium in one or more of the vessels during the bioreaction, (ii) use the values to determine process conditions to maintain substantially uniform values of the two or parameters in the culture medium from vessel-to-vessel among the two or more vessels, and (iii) introduce the culture media to the perfusion vessel through the fluidic inlet, flow the culture media over the biological cells while they are retained in the perfusion vessel, and flow the culture media out the fluidic outlet, to thereby operate in a perfusion mode.

Stated another way, at least one of the fluidically coupled vessels includes a fluidic inlet and a fluidic outlet and the bioreactor system is configured to introduce the fresh culture media to the at least one vessel through the fluidic inlet, allow the flow of the fresh culture media into the bioreactor containing biological cells while they are retained in that vessel, and flow the exhausted culture media out the fluidic outlet, to thereby operate the at least one vessel in a perfusion mode. Various mechanisms may be employed to ensure that the cells remain in the vessel. For example, a fluidic outlet may include a filter or trap configured to prevent the biological cells in the vessel from leaving the at least one vessel or its fluidic outlet. In some implementations, a vessel configured to operate in perfusion mode includes micro-carriers, hollow fiber filter, a cell settler, and/or an acoustic separator, any of which may be employed to retain cells within a perfusion mode vessel.

Any individual one or more of the vessels in the multi-vessel bioreactor system may be configured to operate in perfusion mode. In some implementations, at least two of the fluidically coupled vessels each include a fluidic inlet and a fluidic outlet and the bioreactor system is configured to introduce the fresh culture medium to the at least two vessels through the fluidic inlets, flow the fresh medium into the vessels while the cells are retained in the at least two vessels, and flow the exhausted culture media out the fluidic outlets, to thereby operate the at least two vessels in a perfusion mode. In some instances, one vessel simply supplies the nutrient and oxygen laden media to the perfusion system, thereby acting as a reservoir for new media and to oxygenate and stabilize the fluid returning from the vessel where the perfusion growth process is occurring.

In some implementations, one of the vessels is a master vessel configured to provide culture media to the at least one other vessel through the fluidic inlet to provide perfusion. Further, the control system and master vessel may be together configured to maintain values of dissolved oxygen concentration, temperature, and pH in the culture medium in the master vessel and in the at least one vessel. In certain perfusion-configured bioreactor systems, the master vessel includes a mixing system, while the at least one vessel does not include any mixing system.

Methods of Scaling a Bioprocess

As explained, the disclosed concepts facilitate scaling a bioprocess working volume from that of a small-scale bioreactor to that of a large-scale bioreactor. In certain embodiments, a scaling process initially involves determining appropriate process conditions for performing the bioprocess in a test vessel having a relative small working volume (e.g., no greater than about 700 liters). Examples of process conditions that may be designed for the test vessel include values of two or more parameters characterizing culture medium in the vessel during the bioprocess. Relevant parameters discussed above including temperature, pH, dissolved oxygen concentration, etc. may be employed. After determining process conditions for the test vessel, the scaling process involves designing a bioreactor system having a control system and two or more fluidically connected production vessels. Each of production vessels has a working volume that is similar to that of the test vessel (e.g., within the range of the turndown ratio for the test vessel. In some embodiments, each production vessel has a working volume that is between about 0.7 and 1.5 times the working volume of the test vessel. In certain embodiments, the sum of the working volumes of the two or more production vessels is at least about 2 times larger than the working volume of the test vessel.

In certain embodiments, the design process involves designing the control system to maintain substantially uniform values of one or more parameters, from production vessel to production vessel, during the intended to bioreaction. As discussed above, a suitable control system may (i) read or receive production values of the two or more parameters characterizing the culture medium in one or more of the two or more vessels during the bioprocess, (ii) use the read or received production values to determine an adjusted flow rate of the culture medium between the two or more production vessels to maintain substantially uniform production values of the two or parameters in the culture medium from vessel-to-vessel among the two or more production vessels during the bioprocess, and (iii) control one of the fluid transfer devices disposed between the two or more production vessels to adjust the flow rate as determined in (ii). It should be noted that such control loop keeps conditions substantially the same from vessel-to-vessel in the bioreactor system, as opposed to a different control loop, that may be implemented in a master vessel that keeps the parameter values within the ranges required (absolute ranges).

Often the process of designing the control system for large-scale bioreactor system involves designing the control system to maintain, during the bioprocess, the production values of the two or more parameters to be substantially equal to the test values of the two more parameters.

After designing the production vessels and the control system, the process involves actually constructing and/or arranging the two or more production vessels and the control system to as specified to produce the large-scale bioreactor. Finally, the bioprocess may be performed in the large-scale bioreactor. In some implementations, the large-scale bioreactor system is configured to permit bidirectional flow of the culture medium between two of the production vessels, and/or the two or more production vessels are arranged in closed loop.

During the bioprocess, the total amount of culture medium in the bioreactor system may increase. For example, the bioprocess may be conducted at a first total working volume of culture medium in the bioreactor, and then the bioprocess may be conducted at a second total working volume of culture medium that is greater than the first total working volume but still uses only the two or more production vessels of the large-scale bioreactor. This may be accomplished by adding culture medium to the bioreactor system before the bioprocess completes. In another approach, at least a portion of the bioprocess may be conducted in the bioreactor, and then, one more additional production vessels are added to or activated in the bioreactor system. Thereafter, the bioreactor system may be operated to at least partially fill the one or more additional production vessels with culture medium from one or more other production vessels of the bioreactor system. Yet another mode of operating involves (i) conducting the bioprocess in the bioreactor system, and then (ii) removing one or more of the two or more production vessels containing culture medium and cells grown in the culture medium. This approach may be appropriate when the cells in a vessel are cultivated for treating a patient.

In certain embodiments, the large-scale bioreactor system includes more than two production vessels—e.g., as explained above, three, four, five, six, or more production vessels—configured to collectively carry out the bioprocess. In certain embodiments, each production vessel has a working volume of no greater than about 500 liters. In some implementations, the ratio of total working volume of the two or more production vessels to the working volume of largest of the two or more production vessels is at least about 3. In certain embodiments, the two or more production vessels are connected in a star configuration or in a closed loop configuration.

In general, the large-scale bioreactor system may have any one or more of the features described elsewhere herein for such systems. For example, each of the two or more production vessels and the test vessel may have a turndown ratio, and the turndown ratios of any one the two or more production vessels and the test vessel may be limited vary by no more than about 20%. Additionally, the control system may be configured to adjust conditions in the two or more production vessels to ensure that the mean pH of the culture medium in the two or more production vessels does not vary from one vessel to another by more than about 0.1 pH units.

In many embodiments, one of the two or more production vessels is a master vessel and the others are satellite vessels, where the master vessel includes a mixing system configured to agitate the culture medium. Any one of the satellite vessels may or may not include a mixing system. In some such embodiments, the master vessel has a larger working volume than any of the satellite vessels. In some implementations, the master vessel includes one or more sensors for the pH, temperature, a cell metabolite concentration, and dissolved oxygen in the culture medium.

What is claimed is:

1. A method of carrying out a bioreaction in a multivessel bioreactor system, the method comprising:
    flowing a culture medium at an initial flow rate through fluidic paths between a master vessel and two or more slave vessels, each of the slave vessels being fluidically coupled in parallel to the master vessel by each of the slave vessels having a separate one of the fluidic paths extending directly from the slave vessel to the master vessel;
    detecting a first culture medium parameter value in the master vessel or the slave vessels with a master sensor coupled to the master vessel;
    transmitting the first culture medium parameter value from the master sensor to a control system in electronic communication with the master sensor;
    determining an adjusted flow rate of the culture medium at the control system based on the first culture medium parameter value; and
    controlling a bidirectional fluid transfer device with the control system to adjust the flow rate of the culture medium through the fluidic paths and maintain a substantially uniform value of the first culture medium parameter value in the master vessel or the slave vessels.

2. The method of claim 1, wherein the bidirectional fluid transfer device includes a two-way fluid transfer device along each of the separate one of the fluidic paths extending directly from the slave vessels to the master vessel, said flow rate of the culture medium comprising a flow rate in a first direction and a flow rate in a second direction;
    the method further comprising controlling each two-way fluid transfer device with the control system to operate each two-way fluid transfer device to adjust both the flow rate in the first direction and the flow rate in the second direction and maintain the substantially uniform value of the first culture medium parameter value in the master vessel or the slave vessels.

3. The method of claim 1, wherein each of the slave vessels includes two or more separate fluidic paths extending directly from the slave vessel to the master vessel,
    the method further comprising controlling the bidirectional fluid transfer device with the control system to adjust the flow rate of the culture medium through each of said two or more separate fluidic paths and maintain a substantially uniform value of the first culture medium parameter value in the master vessel or the slave vessels, such that bidirectional flow of the culture medium occurs between the master vessel and each of the slave vessels.

4. The method of claim 1, the method further comprising controlling a mixing system within the master vessel to agitate the culture medium therein, the mixing system comprising at least a sparger or an impeller.

5. The method of claim 1, wherein the master sensor comprises one or more scales and/or load cells and the first culture medium parameter comprises a volume of the culture medium.

6. The method of claim 1, wherein the substantially uniform value of the first culture medium parameter comprises a mean pH of the culture medium that does not vary from one vessel to another by more than about 0.1 pH units.

7. The method of claim 1, wherein said flowing the culture medium through fluidic paths between the master vessel and the two or more slave vessels is performed in a perfusion mode, the method further comprising:
   introducing the culture medium from the master vessel to each of the slave vessels through a fluidic inlet of each of the slave vessels;
   exchanging the culture medium in each of the slave vessels while retaining biological cells in the slave vessels; and
   flowing the culture medium out of a fluidic outlet of each of the slave vessels.

8. The method of claim 7, wherein the fluidic outlet comprises a filter configured to prevent the biological cells in the slave vessel from leaving the slave vessel and the fluidic outlet.

9. The method of claim 1, wherein the first culture medium parameter value comprises one or more of pH, temperature, a cell metabolite concentration, and dissolved oxygen concentration of the culture medium.

10. The method of claim 1, wherein controlling the bidirectional fluid transfer device with the control system maintains a substantially uniform value of dissolved oxygen concentration, cell metabolite concentration, temperature, or pH in the culture medium in the slave vessels.

11. The method of claim 1, further comprising:
   detecting a second culture medium parameter value in at least one of the slave vessels with a slave sensor coupled to the at least one of the slave vessels;
   transmitting the second culture medium parameter value from the slave sensor to the control system in electronic communication with the slave sensor;
   determining an adjusted flow rate of the culture medium at the control system based on the first and second culture medium parameter value; and
   controlling the bidirectional fluid transfer device with the control system to adjust the flow rate of the culture medium and maintain a substantially uniform value of the first and second culture medium parameter value in the master vessel and the slave vessels.

12. The method of claim 1, wherein said two or more slave vessels comprises three or more slave vessels.

13. The method of claim 1, wherein the ratio of total working volume of the slave vessels to the working volume of the master vessel is at least about 3.

* * * * *